United States Patent
Herbert et al.

(10) Patent No.: US 11,304,958 B2
(45) Date of Patent: Apr. 19, 2022

(54) MULTIDENTATE PHENANTHRIDINE-CONTAINING LIGAND FRAMEWORKS AND THEIR PLANAR MONOFUNCTIONAL PLATINUM COMPLEXES FOR CANCER TREATMENT

(71) Applicant: UNIVERSITY OF MANITOBA, Winnipeg (CA)

(72) Inventors: David E. Herbert, Winnipeg (CA); Issiah B. Lozada, Winnipeg (CA); Bin Huang, Winnipeg (CA); Yaorong Zheng, Kent, OH (US); Zihan Qiu, Kent, OH (US)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 17/041,592

(22) PCT Filed: May 24, 2019

(86) PCT No.: PCT/CA2019/050706
§ 371 (c)(1),
(2) Date: Sep. 25, 2020

(87) PCT Pub. No.: WO2019/222854
PCT Pub. Date: Nov. 28, 2019

(65) Prior Publication Data
US 2021/0052601 A1    Feb. 25, 2021

Related U.S. Application Data

(60) Provisional application No. 62/676,397, filed on May 25, 2018.

(51) Int. Cl.
*A61K 31/555* (2006.01)
*A61K 45/06* (2006.01)

(52) U.S. Cl.
CPC ............ *A61K 31/555* (2013.01); *A61K 45/06* (2013.01)

(58) Field of Classification Search
CPC .............................. A61K 31/555; A61K 45/06
See application file for complete search history.

(56) References Cited

FOREIGN PATENT DOCUMENTS

| WO | WO-2012177935 A1 | * | 12/2012 | ........... C07F 15/0093 |
| WO | WO-2014043243 A2 | * | 3/2014 | ........... C07F 15/0093 |

OTHER PUBLICATIONS

Pavan Mandapati, et al, Phenanthradine-Containing Pincer-like Amido Complexes of Nickel, Palladium, and Platinum, 56 Inorg. Chem. 3674 (Year: 2017).*

* cited by examiner

*Primary Examiner* — Sean M Basquill
(74) *Attorney, Agent, or Firm* — Michael R Williams; Ryan W Dupuis; Ade & Company Inc.

(57) ABSTRACT

Described herein is the development of synthetic routes to produce a wide variety of substituted phenanthridines, specifically, multidentate phenanthridine-containing ligand frameworks capable of anchoring to Pt via more than one binding site and with the phenanthridinyl moiety co-planar to the coordination plane of Pt. The multidentate chelation is designed to attenuate the reactivity of the platinum complex in vivo, and ultimately help mitigate side effects. In addition, the geometry of phenanthridine binding to the metal centre is altered compared to in phenanthriplatin, thanks to the constraints of the ligand geometry. By enforcing coplanar binding with the metal's square planar coordination plane, these compounds exhibit altered modes of activity, and should hence enhance/change the spectrum of activity of our prodrug candidates compared with phenanthriplatin.

14 Claims, 12 Drawing Sheets

L4 (R[1] = R[2] = R[3] = CH₃)
L5 (R[1] = tBu, R[2] = H, R[3] = CF₃)
L6 (R[1] = CF₃, R[2] = H, R[3] = CF₃)

MULTIDENTATE PHENANTHRIDINE-CONTAINING LIGAND FRAMEWORKS AND THEIR PLANAR MONOFUNCTIONAL PLATINUM COMPLEXES FOR CANCER TREATMENT

PRIOR APPLICATION INFORMATION

The instant application claims the benefit of US Provisional Patent Application Filed May 25, 2018 and entitled "MULTIDENTATE PHENANTHRIDINE-CONTAINING LIGAND FRAMEWORKS AND THEIR PLANAR MONOFUNCTIONAL PLATINUM COMPLEXES FOR CANCER TREATMENT", the entire contents of which are incorporated herein by reference.

BACKGROUND OF THE INVENTION

Cisplatin (2) and related platinum (Pt) based drugs are indisputably important in current cancer treatment (29). Since the clinical approval of cisplatin [cis-diaminedichloroplatinum(II)], a coordination complex of platinum(II) ($Pt^{2+}$) with cis-disposed chloride and amine ligands, the cure rate for testicular cancer has jumped from 10% to 90% (1). Cisplatin (2) is now used in an estimated 50% of cancer patients, to treat testicular, ovarian, bladder, lung, head/neck, esophageal, cervical and uterine cancers, inter alia, and as second-line chemotherapy in advanced solid tumours (3). This highlights the transformation cancer treatment has undergone as a result of the clinical implementation of inorganic coordination complexes as chemotherapeutics. Beyond cisplatin, however, the list of Food and Drug Administration (FDA)-approved platinum-based antitumor drugs contains only a small number of additional compounds: carboplatin [c/s-diamine(1,1-cyclobutanedicarboxylato)platinum(II)], oxaliplatin [(R,R)-1,2-diaminocyclo-hexane)oxalate-platinum(II)], with two more (satraplatin and picoplatin) under consideration or in advanced clinical trials (FIG. 1) (1).

The activity of Pt-based anticancer agents is attributed to the formation of intrastrand and interstrand DNA cross-links mediated by covalent binding of Pt with purine nucleobases, inhibiting transcription and inducing apoptosis (4). Platin chemotherapy, however, can be limited by severe side effects due to off-target activity, and reduced efficacy due to acquired or intrinsic resistance in certain types of cancers. Side effects can be severe, and include emesis, alopecia, nausea, kidney damage, myelosuppression and peripheral neuropathy (1). The promise and limitations of platin drugs clearly highlight the need for new platinum-based chemotherapeutics.

One strategy for increasing potency while mitigating side effects and expanding the spectrum of activity is to search out platinum-based drugs that operate by novel mechanisms of action (5). The regulatory-approved platins (cisplatin, carboplatin and oxaliplatin; see also FIG. 1) share the same core structure: all are square-planar metal complexes of four-coordinate Pt in the +2 oxidation state typical of $d^8$ Pt(II) centers, with two firmly-bound "non-leaving" ligands or strongly coordinating ligands (amines in blue; ammonia, or $NH_3$, in cisplatin and carboplatin; trans-1,2-diaminocyclohexane, or DACH, in oxaliplatin) neighbouring one another in a cis orientation (see FIGS. 1 and 12). An additional two ligands, which are labile (in red; chlorides, $Cl^-$, in cisplatin; cyclobutanedicarboxylate in carboplatin; oxalate in oxaliplatin), complete the coordination sphere. These latter ligands can be displaced by water under certain or relevant physiological conditions to generate the active pharmaceutical ingredient (API): mono- and b/s(aqua) complexes $c/s$-$[Pt(NH_3)_2Cl(OH_2)]^+$ and $c/s$-$[Pt(NH_3)_2(OH_2)_2]^{2+}$. These cations are highly reactive, and bind to purine DNA nucleobases (e.g., guanine, G). By binding two nearby guanines in what has been termed "bifunctional cross-linking", these cations can cause 1,2-intrastrand cross-links that deform DNA strands, blocking transcription and triggering downstream cell-death pathways (FIG. 2) (6).

In comparison, monofunctional DNA-binding platinum anticancer drug candidates contain only a single labile ligand, and as such can only bind to DNA through a single coordination site opened up by a vacating chloride (7). Nevertheless, monofunctional platinum complexes such as phenanthriplatin ($[c/s$-$R(NH_3)_2(phenanthridine)Cl][NO_3]$) have been shown to display significant antineoplastic activity (10). Thus, pyriplatin (FIG. 1, bottom) binds to DNA at a single N7 position of guanine residues and in turn, does not significantly distort the double helix (8). Biochemical interactions of monofunctional platins are therefore quite different than the significant DNA bending which occurs at 1,2-intrastrand cross-links that follow treatment with bifunctional chemotherapeutics such as cisplatin (6). Moreover, as the biochemical interactions of monofunctional platinum complexes differ from bifunctional ones, they also can show a distinct spectrum of action and the potential for altered resistance/side-effect profiles. Such platinum-based chemotherapeutics are therefore of increasing interest.

Following on from pyriplatin, which is reportedly ten-fold less potent than cisplatin or oxaliplatin (9), Lippard and coworkers have disclosed a series of monofunctional platin drug candidates including "phenanthriplatin" (10), which displays significant anti-neoplastic properties, attributed to transcription inhibition followed by apoptosis (9). Importantly, phenanthriplatin shows a different spectrum of activity compared with cisplatin (11, 12). Interestingly, similar to cisplatin, but unlike less active monofunctional drug candidates, phenanthriplatin also induces bacterial filamentation and initiates lysis in lysogenic bacteria, supporting the hypothesis that its biological activity is mediated by interactions with DNA (13). An additional distinguishing feature of monofunctional platins such as phenanthriplatin is the near perpendicular orientation of the N-heterocyclic ligand (phenanthridine) with respect to the coordination plane of platinum. Complexes of platinum in the (+2) oxidation state typically exhibit square planar geometries, as a result of the stabilizing effect of this geometry's ligand field on the transition metal's occupied d orbitals (14). Coupled with the asymmetry of phenanthridine, this results in phenanthriplatin being chiral, with racemization possible upon rotation about the R—N(phenanthridine) bond.[15] The chirality of pharmacological agents can be critical to their activity, as different enantiomers typically display different activity due to changes in their interactions with inherently chiral biological systems. The formulation of oxaliplatin in clinical use, for example, contains only a single enantiomer (38),] as the R,R isomer of trans-diaminocyclohexaneoxalatoplatinum(II) shows enhanced activity compared to the S,S form (39). In the case of phenanthriplatin, model complex studies suggest that while racemization is rapid enough to preclude requiring administration of a single enantiomer, there is a preference for diastereomer formation upon binding to DNA (15). Achiral structures that, as a result, do not form diastereomers with differing stabilities can avoid the need for racemization under physiological conditions, potentially enhancing the efficacy of the chemotherapeutic.

While phenanthriplatin shows heightened antineoplastic activity compared to cisplatin, pyriplatin ([c/s-R(NH₃)₂(pyridine)Cl][NO₃], in which the tricyclic phenanthridine (3,4-benzoquinoline) is replaced with a smaller N-heterocycle pyridine, is ten-fold less potent (9). Single-molecule DNA-stretching experiments revealed a two-step binding process for phenanthriplatin, where rapid unwinding of DNA triggered by intercalation of the phenanthridine unit is followed by slow covalent modification (30). The smaller AZ-heterocycle pyridine does not associate as effectively with duplex DNA prior to covalent binding, resulting in lower efficacy. The disposition of the N-heterocycle to the labile ligand is also important; DNA intercalation of the stereoisomer of phenanthriplatin with the heterocycle trans disposed to the chloride ([<rans-R(NH₃)₂(phenanthridine)Cl][NO₃]) (31) competes with, rather than enhances, covalent binding, reducing the number of R-DNA adducts formed (30). Trans-phenanthriplatin is nevertheless still an effective anticancer agent, with very different activity compared to phenanthriplatin (31). This is not true of fransplatin compared with cisplatin.

A distinguishing feature of both phenanthriplatin and trans-phenanthriplatin is the orientation of the phenanthridine ligand with respect to the coordination plane of platinum. This is nearly orthogonal in the c/s isomer (dihedral angle ~89°) (10) but less so in trans-phenanthriplatin (~67°) (31). Coupled with the asymmetry of phenanthridine (3,4-benzoquinoline) with respect to the position of benzannulation relative to the nitrogen atom, phenanthriplatin is chiral (15). While racemization upon rotation about the R—N (phenanthridine) bond is rapid enough to preclude requiring administration of a single enantiomer, there is a preference for diastereomer formation upon binding to DNA (15). Forcing the phenanthridine ring coplanar with the metal coordination plane would obviate this chirality and raises the interesting question of whether "in-plane" phenanthriplatin analogs would still show enhanced anticancer efficacy or act in the same fashion as conventional platinum-intercalator antitumor agents (32).

SUMMARY OF THE INVENTION

According to a first aspect of the invention, there is provided an anti-cancer compound comprising a compound of formula (I) or a compound of formula (I):

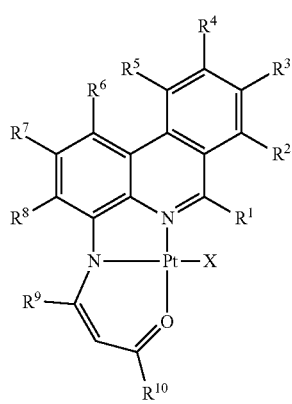

(I)

wherein:
X is a halide, a nitrate, a carboxylate or an anionic ligand;
$R^1$-$R^8$ are individually H, $C(CH_3)_3$, $CH_3$, $CF_3$, Cl, Br, F, C(O)H or OR, where R is an alkyl or aryl; and
$R^9$ and $R^{10}$ are individually H, $CF_3$ or $CH_3$.

According to another aspect of the invention, there is provided a method of modifying a compound of formula (I) as set forth above comprising:
providing a compound of formula (I) wherein at least one of $R^1$-$R^8$ is $CH_3$; and
subjecting the compound to oxidizing conditions such that the at least one $CH_3$ is converted to C(O)H.

According to another aspect of the invention, there is provided a method of treating cancer comprising administering to an individual in need of such treatment an effective amount of a pharmaceutical compound or composition comprising or consisting essentially of or consisting of a compound of formula (I) as set forth above.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is the construction of multidentate phenanthridine-containing ligand frameworks capable of anchoring to Pt via more than one binding site. As in oxaliplatin (33), and distinct from in phenanthriplatin (10), multidentate chelation is designed to attenuate the reactivity of the platinum complex in vivo, and ultimately help mitigate side effects. In addition, the geometry of phenanthridine binding to the metal centre is altered compared to in phenanthriplatin, thanks to the constraints of the ligand geometry. By enforcing a coplanar binding with the metal's square-planar coordination plane, these compounds should exhibit altered modes of activity, and hence enhance/change the spectrum of activity, of our prodrug candidates compared with phenanthriplatin, as demonstrated by the supporting in vitro data provided. In addition, equipping prodrugs with fluorophores that can act as optical reporters to aid monitoring of drug delivery is an appealing way to combine therapy with diagnostics ("theranostics") and aid in drug development. The invention design herein disclosed also show efficient solution-state emission, suggesting the possibility of pre-equipping platinum prodrugs with a luminescent reporter tag for theranostic purposes (34).

Figure 1:
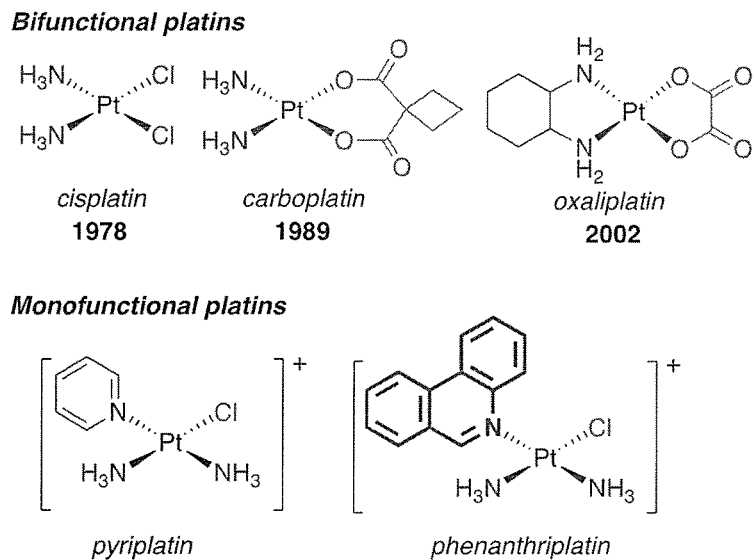
FIG. 1. Top: Bifunctional chemotherapeutic agents and their earliest date of regulatory approval in North America. Bottom: Monofunctional drug candidates pyripiatin and phenanthriplatin.

As discussed herein, we have developed synthetic methodologies for incorporating phenanthridinyl units (bolded in FIG. 1), the unique chemical moiety in phenanthriplatin, into ligand frameworks in order to explore the coordination chemistry of these frameworks with transition metals (16, 17). Motivated at first by an interest in the impact of site-selective benzannulation on the photophysical properties and reactivity of late transition metal complexes of these ligands (18), we developed synthetic routes to produce a wide variety of substituted phenanthridines, suitable for further elaboration into ligand frameworks. Considering the efficacy of phenanthridine-containing platin drug candidates (e.g., phenanthriplatin) may be attenuated by chirality and the kinetics of racemization (15), this invention discloses "in-plane" phenanthridine-platin, geometrically restricted platin derivatives as monofunctional chemotherapeutics.

In this work, we describe the construction of multidentate phenanthridine-containing ligand frameworks capable of anchoring to Ft via more than one binding site. As in oxaliplatin (FIG. 1), multidentate chelation is designed to attenuate the reactivity of the platinum complex in vivo, and ultimately help mitigate side effects. In addition, the geometry of phenanthridine binding to the metal centre is altered compared to in phenanthriplatin, thanks to the constraints of the ligand geometry. By enforcing coplanar binding with the metal's square planar coordination plane, these compounds exhibit altered modes of activity, and should hence enhance/change the spectrum of activity of our prodrug candidates compared with phenanthriplatin. Moreover, phenanthridine itself is the molecular core of the widely used DNA stain ethidium bromide (19), which operates via intercalation of its extended planar structure into DNA. While not wishing to be bound to a particular theory or hypothesis, we anticipate that intercalation plays a prominent role in the anti-neoplastic behaviour of the proposed prodrug candidates.

An intercalative mechanism has been ruled out for phenanthriplatin on the basis of experiments examining the affinity of ethidium bromide for calf thymus DNA in the presence of phenanthriplatin, which revealed non-competitive inhibition of ethidium by phenanthriplatin (40). The compounds described here therefore represent a fundamentally different class of phenanthridine-platinum drug candidates, and therefore with important functional differences as well, compared to phenanthriplatin.

Moreover, phenanthridine derivatives exhibit efficient solution fluorescence from a $\pi$-$\pi^*$ singlet excited state, thanks to an extended $\pi$-conjugated structure with lower ($C_{2v}$) symmetry compared to the all-hydrocarbon analog phenanthrene.[20] We therefore also report on the emissive properties of the platinum compounds as a strategy to pre-equip platinum prodrugs with a luminescent reporter tag. Strongly emissive platinum compounds are useful reagents for in vivo imaging using techniques such as time-resolved emission imaging (41). Tracking the fate of bioactive platin drug candidates in vitro and in vivo using emission spectroscopy is therefore impactful for developing and understanding modes of action, combining both therapeutic and diagnostic elements into a "theranostic" agent.

Furthermore, from a commercial perspective, intercalation of NNOPt complexes may further allow for staining similar to the wide use of ethidium bromide as an intercalative dye, with the important difference that emission from ethidium is fluorescence, that is from a singlet excited state, while the NNOPt complexes disclosed here exhibit phosphorescent emission (from a triplet excited state). Triplet emission allows for harvesting a greater number of photons compared to singlet emitters, and thus could represent a marked improvement over ethidium (phenanthridine) based organic dyes with respect to use as a tool for studying biochemical pathways. This is significant both for examples of the invention that exhibit strong cytotoxicity (activity as anti-neoplastics) for chemotherapy, and also for modifications that retain strong emission (high quantum yields) while exhibiting lower toxicity (see, for example, (41)) Furthermore, modifications of the substituents on the ligand backbone are demonstrated here to modify biochemical activity, and thus both highly active (cytotoxic) and less active congeners are accessible, using the synthetic approach disclosed herein.

The non-obvious and unique feature of the compounds of the invention invention in the development of novel "theranostic" platin prodrugs with potentially novel modes of action in cancer chemotherapy that additionally bear optical fluorophore reporters, is the incorporation phenanthridine into multidentate ligand frameworks that alter the binding geometry of the N-heterocycle, and further augments the anti-cancer activity by providing a planar site for DNA intercalation in addition to Pt-based cross-linking, while simultaneously showing enhanced luminescence properties.

Figure 10:
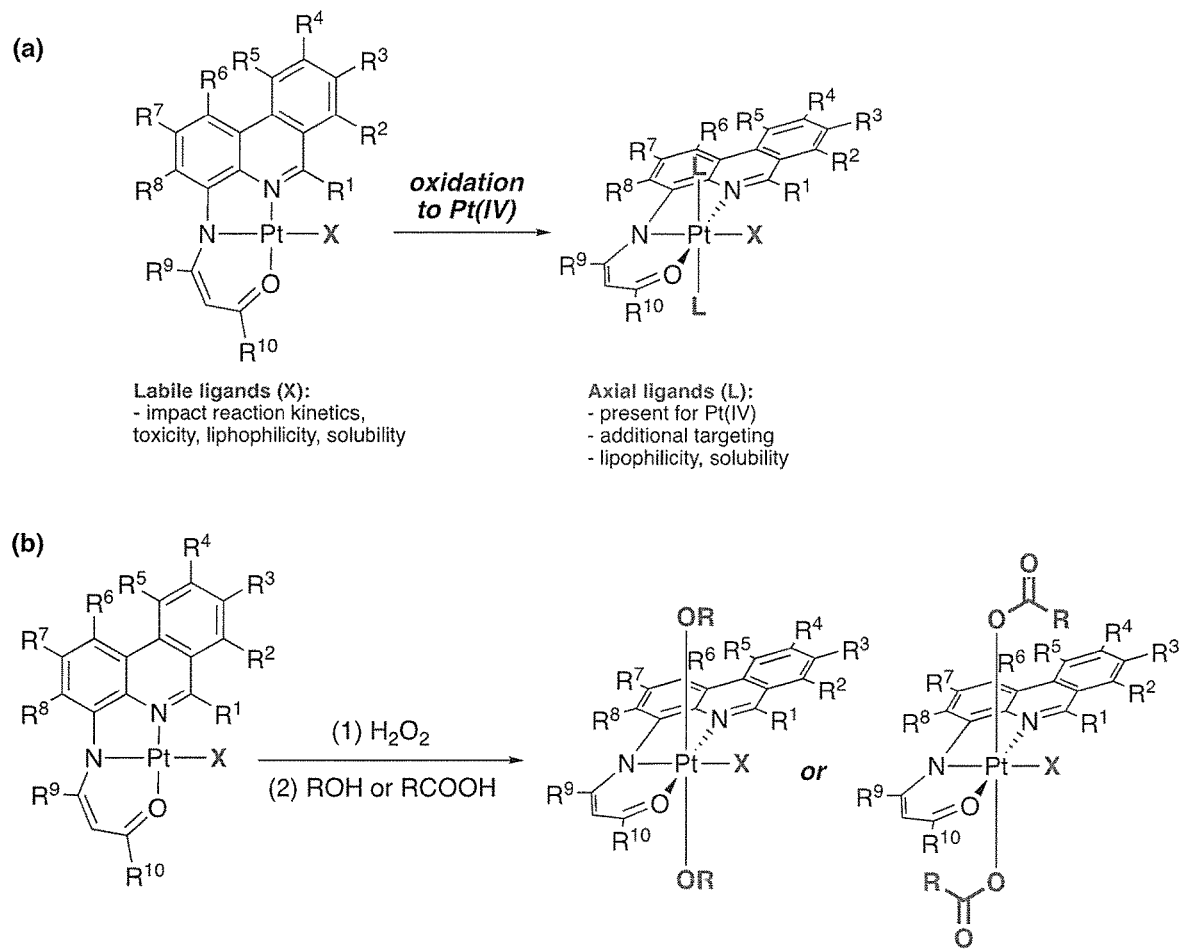
FIG. 10. Proposed additional modifications.
Figure 17:
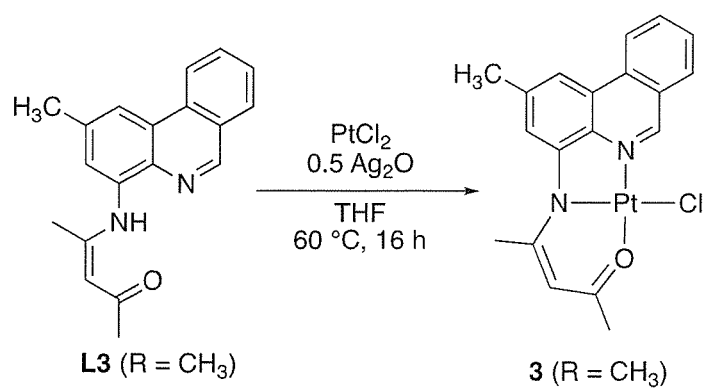
FIG. 17. Methyl analog of proligand and Pt complex.
Figure 18:
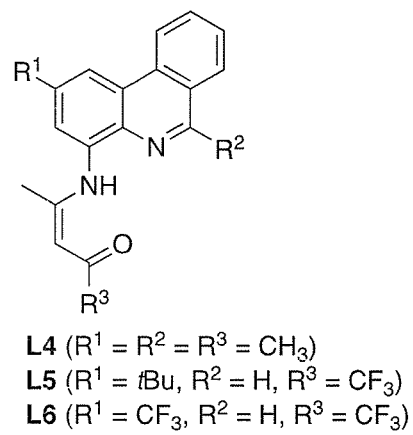
FIG. 18. Additional proligand modifications prepared.

Substitution of both the phenanthridinyl ring, as well as the "nac-ac" (NNO) portion of the ligand framework, as well as substitution of the chloride to modify solubility and emissive properties, as well as DNA binding efficacy are all possible modifications as discussed herein and as will be apparent to one of skill in the art. Use of R groups to enhance encapsulation or conjugation to drug-delivery vehicles such as nanoparticles, biocompatible polymers and the like may also be carried out within the scope of the invention, as discussed herein. The position of R groups in the 4-position of the phenanthridinyl arm, para to the N donor can be expected not to influence the coordinating properties of the proligands, as evidenced by similar yields of reaction for the synthesis of 1 (bearing an electron-releasing tBu group) and 2 (bearing an electron-withdrawing $CF_3$ substituent). Thus, variants bearing, for example, lipophilic $C_{12}$ chains or targeting groups will bear physical similarities to the compounds reported with respect to the Pt coordination environment, and indicates that they will have similar activities in vitro to 1 and 2. Other changes that would be expected to enhance/alter solubility, but otherwise have no effect would be inclusion of water-solubilizing groups including long alkyl chains with charged moieties at the far terminus such as sulfonates. Tethering such units to the active Pt core via long chains would not impact the sterics surround phenanthridine and therefore likely not impact the mechanism of action. With these possible modifications in mind, we also provide characterization data for proligands L3-L6 and platinum complex 3, shown in FIGS. 10,17 and 18.

Endless variations of platinum drug candidates are constantly being sought or are under investigation. The main competitor is the simple, orthogonal phenanthridine analog, phenanthriplatin. The key non-obvious invention here is the "in-plane" geometric restriction of the phenanthridinyl unit via incorporation into a multi-dentate ligand framework. In addition, modifications to improve drug delivery and efficacy are also possible. For example, oxidation to Pt(IV) would enable accommodation of additional ligands[7] that may enhance solubility and allow for incorporation of targeting units such as antibodies. Similarly, encapsulation within larger biomolecule carriers could also be used to enhance delivery (25). Upon reduction in vivo to Pt(II), dissociation of the additional axial ligands would re-introduce the planar structure key to the activity of NNOPt type and related complexes. According to an aspect of the invention, there is provided an anti-cancer compound or drug comprising or consisting of or consisting essentially of a compound of formula (I) or a compound of formula (I):

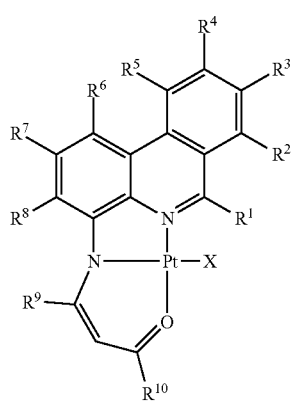

(I)

wherein:

X is a halide, a nitrate, a carboxylate or an anionic ligand;

$R^1$-$R^8$ are individually H, $CH_3$, tBu, $CF_3$, Cl, Br, F, C(O)H or OR, where R is an alkyl or aryl; and $R^9$ and $R^{10}$ are individually H, $CF_3$ or $CH_3$.

In the examples provided below, $R^1$-$R^6$ and $R^8$=H, $R^7$=$CF_3$ or tBu, and $R^9$-$R^{10}$=$CH_3$.

Using the synthetic route presented in Scheme 1, $R^1$-$R^8$ may individually be $CH_3$, $CF_3$, Cl, Br, F, C(O)H (via oxidation of any R=$CH_3$ using $SeO_2$ or another suitable oxidation pathway), OR (R=alkyl, aryl).

As will be apparent to one of skill in the art, following oxidation, when a single aldehyde moiety is present (e.g., as one of $R^1$-$R^8$, where other R groups are substituents stable to oxidation), conversion of this aldehyde C(O)H to amide, carboxylic acid or ester groups is then possible. Positioning the aldehyde as $R^7$ or $R^4$ is considered to present the most synthetically accessible option, based on the synthetic route described herein.

As discussed herein, amide C(=O)$NH_2$ and carboxylic acid moieties can then be used to conjugated biochemical targeting tags (protein or peptide tags, DNA, oligonucleotides, or siRNA) (35) or solubilizing biocompatible polymer residues (e.g., polyethylene glycol—PEG) (42) to engage active targeting of specific biological structures or to modify solubility properties to influence uptake by passive targeting, for example, via conjugation to macromolecular chains to turn on passive targeting by the EPR (enhanced permeability and retention) effect (43), whereby increasing the molecular weight of a drug is used to enhance uptake and retention in tumour tissue (44).

Modifications of the acetyl acetone reagent including $R^9$=$R^{10}$=$CF_3$; $R^9$=$CF_3$, $R^{10}$=$CH_3$; $R^{10}$=$CF_3$, $R^9$=$CH_3$ to introduce perfluoroalkyl groups are accessible through use of hexafluoroacetylacetone or trifluoroacetylacetone in place of acetylacetone (Scheme 2). As will be appreciated by one of skill in the art, incorporation of fluoroalkyl groups will modify the hydrophobicity of the molecules and therefore the cellular uptake, and potentially the bioactivity, of the platinum complexes, as well as modulating their photophysical properties, similar to the improved properties and activity observed for 2 compared with 1, as discussed below.

Modification of the labile X ligand from chloride to other halides, nitrates, carboxylates or other anionic ligands is also feasible, which can influence solubility and the rate of aquation of the platinum complexes.

In some embodiments of the invention, $R^1$=$R^7$=$CH_3$, $R^{2-6}$=$R^8$=H;

In other embodiments of the invention, $R^{1-8}$=H;

In yet other embodiments of the invention, $R^7$=C(=O)H (aldehyde), $R^{1-6}$=$R^8$=H.

In some embodiments of the invention, the compound is selected from the group consisting of: $R^7$=tBu; $R^7$=$CF_3$; $R^7$=$CH_3$; $R^1$=$CH_3$, $R^7$=$CH_3$, $R^{10}$=$CH_3$; $R^1$=H, $R^7$=tBu, $R^{10}$=$CF_3$; and $R^1$=H, $R^7$=$CF_3$, $R^{10}$=$CF_3$.

Additional modifications to the invention include oxidation of the NNOPt complexes from Pt(II) to Pt(IV). In these congeners, the coordination environment of the metal center would change from four-coordinate, square planar to six-coordinate, octahedral, with two additional anionic ligands (L in FIG. 10a) binding to platinum upon oxidation. The planar, multidentate nature of the NNO ligand continues to enforce a planar geometry of this moiety even in the higher oxidation state. Pt(IV) compounds are kinetically more inert towards ligand substitution (e.g., to aquation which is attributed to the onset of activity for most platin drugs) and thus the Pt(IV) modifications are anticipated to reduce off-target toxicity due to interactions with off-target biomolecules, with in situ reduction to Pt(II) used to turn on anti-neoplastic character (45).

In addition, the two added ligands (L in FIG. 10a) provide additional opportunities to modify the physical and chemical properties of the prodrug, while introducing further attachment sites for targeting units, linkers for conjugation to nanoparticles and carrier molecules for enhancing active or passive targeting. These targeting units can include those listed above, made possible by aqueous oxidation using hydrogen peroxide, followed by nucleophilic substitution with carboxylic acid or alcohol residues (FIG. 10b). Also feasible are carboxylic acid anhydrides, isocyanates, acid chlorides or pyrocarbonates, to yield platinum(IV) carboxylates, carbamates or carbonates, ((45) and references therein) or cyclic diacid anhydrides to yield dicarboxylates with terminal carboxylic acid moieties amenable to further functionalization using ester or amide-bond forming reactions (46).

Ligand and Complex Synthesis

Figure 3:
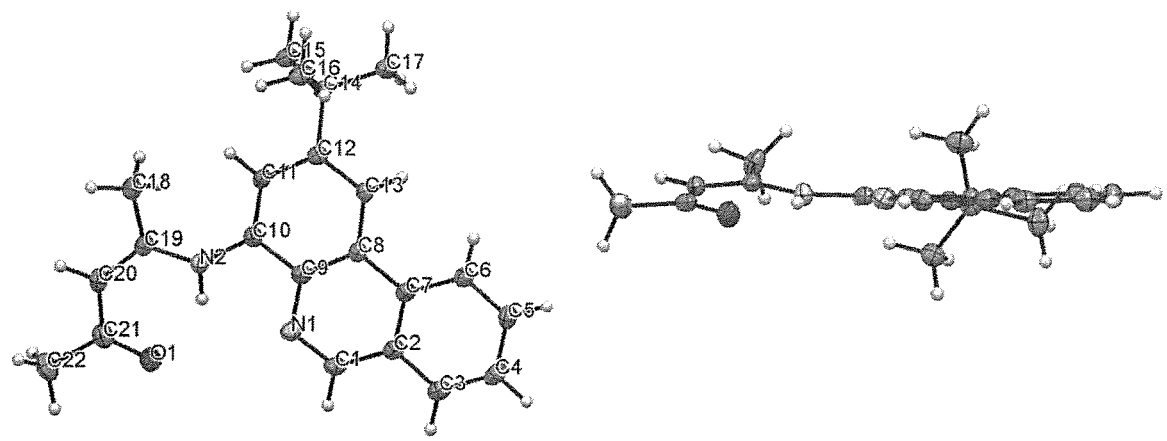
FIG. 3. ORTEP[23] of L1 with thermal ellipsoid shown at 50% probability levels. Two views are shown. Selected bond distances (Å): C(1)-N(1) 1.303(3), C(9)-N(1) 1.380(3), C(8)-C(9) 1.410(3), C(7)-C(8) 1.451(3), C(1)-C(2) 1.423(3), C(2)-C(7) 1.411(3), C(10)-N(2) 1.396(3), C(19)-N(2) 1.363 (3), C(19)-C(20) 1.370(3), C(20)-C(21) 1.433(3), C(21)-O 1.244(3). Note the particularly short C(21)-O distance is consistent with the keto tautomer discussed in the text.
Figure 13:
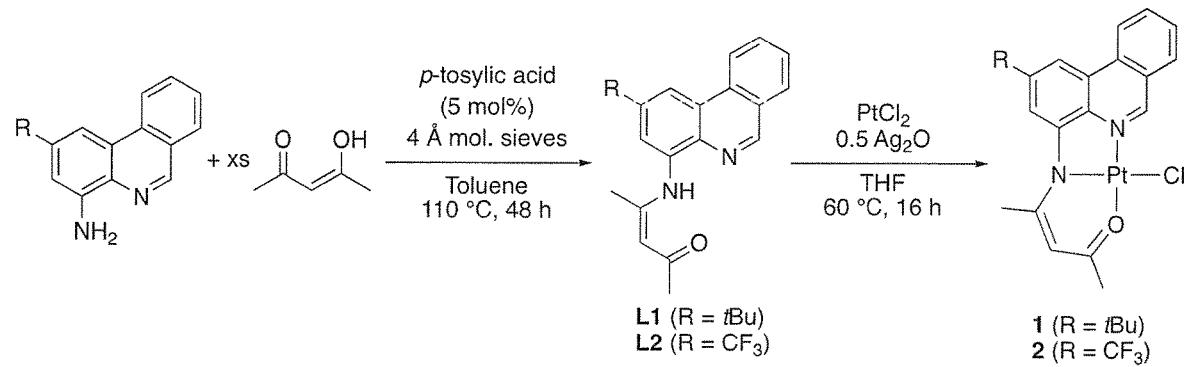
FIG. 13. Proligand and platinum complex synthesis.

Multidentate proligands containing phenanthridinyl units were prepared via acid-catalyzed condensation of 4-aminophenanthridines with acetyl acetone (FIG. 13). The electronic influence of the substituent in the 2-position did not significantly influence the reaction, and proligands bearing electron-releasing tBu groups (L1) and electron-withdrawing groups (L2) could be isolated in similar yields (~64%). This synthetic protocol is therefore amenable to a broad range of chemical functionalization, including the installation of lipophilic tails, amide units or phosphate units for attachment of antibodies or other targeting groups (35). Single-crystals of the proligand L1 suitable for X-ray crystallographic analysis were grown from mixtures of diethylether and chloroform (FIG. 3). The structural metrics, in particular the short C(21)-O(1) bond distance of 1.244(3) Å, are consistent with the keto/enamine tautomer. This assignment was corroborated by comparing solution NMR and IR parameters with related compounds (22).

Figure 4:
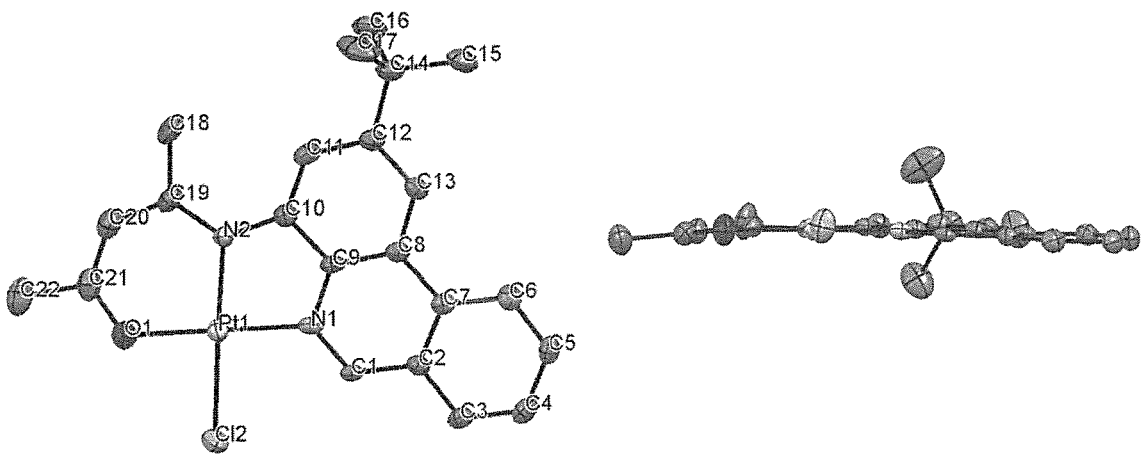
FIG. 4. ORTEP[23] of 1 with thermal ellipsoids shown at 50% probability levels. Two views are shown. Selected bond distances (Å): N(1)-Pt 1.978(4), N(2)-Pt 1.991(3), O—Pt 1.979(3), Pt—Cl 2.3137(12), C(10)-N(2) 1.419(6), C(19)-N(2) 1.357(6), C(19)-C(20) 1.402(7), C(20)-C(21) 1.376(8), C(21)-O 1.278(6). Selected bond angles (°): N(1)-Pt—N(2) 82.68(14), N(1)-Pt—O 178.49(15), N(1)-R—Cl 95.34(10), N(2)-Pt—O 97.61 (15), N(2)-Pt—Cl 176.70(11), O—Pt—Cl 84.44(11).

Once in hand, metallation of the proligands was carried out using $PtCl_2$ in the presence of 0.5 equivalents of silver oxide in THF at elevated temperatures. Again, the electronics of the phenanthridinyl unit did not impact the progress of the reaction, and platinum complexes 1 and 2 were isolated as air-stable, orange solids in similar yields (~86-87%). Ligand binding was confirmed by disappearance of the downfield signal attributed to the acidic N—H proton of the proligands (L1:13.44 ppm; L2:13.72 ppm) and a shift in the CH resonance in the 6-position of the phenanthridinyl ring system, which furthermore shows coupling to $^{195}Pt$ (1:10.03 ppm, $^3J_{PtH}$=39 Hz; 2: 10.20 ppm, $^3J_{PtH}$=39 Hz). A similar deshielding effect was observed for complexes of bis(phenanthridinyl)amido and (phenanthridinyl)(quinonlinyl)amido ligands (17). Alternative preparations using oxygenous or nitrogenous Brönsted bases (e.g., $NEt_3$ or NaO/Bu) in place of $Ag_2O$ were similarly successful in generating the target platinum complexes. Single-crystals suitable for crystallographic analysis of 1 were also obtained. The solid-state structure (FIG. 4) confirms co-planarity of the phenanthridinyl moiety and the coordination plane of platinum, with an angle of only 3.5°. The short C(21)-O(1) of 1.278(6) Å is consistent with retention of the keto/enamide structure upon coordination to Ft.

Electronic Absorption and Photoluminescence

Figure 5:
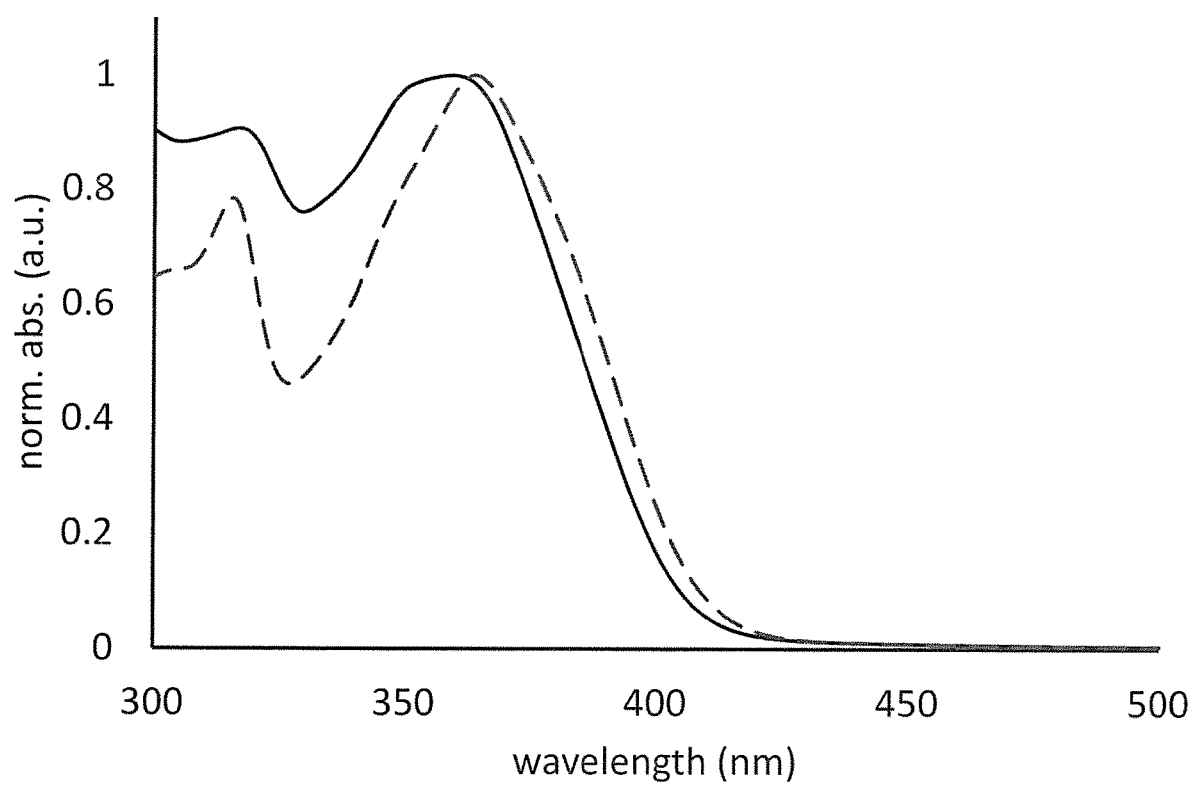
FIG. 5. Normalized absorbance spectra of L1 (solid, black line) and L2 (red, dashed line) in $CH_2Cl_2$ ([ ]=100 μM, $N_2$-saturated).
Figure 6:
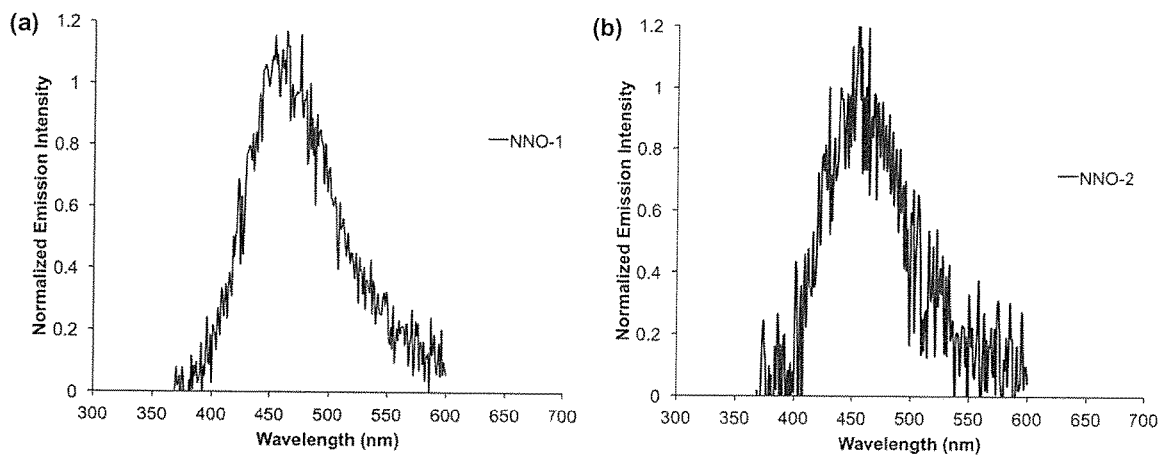
FIG. 6. Normalized emission spectra of (a) L1 and (b) L2 in $CH_2Cl_2$ ([ ]=100 μM, $N_2$-sat.), 3 nm band pass, average of 5 runs.

Proligands L1 and L2 are both bright yellow, crystalline solids, and give yellow solutions, with a broad absorption just at the edge of the visible range (FIG. 5). The proligands are also weakly emissive in solution, attributable to fluorescence from a π-π* singlet excited state associated with the phenanthridine unit (20). Steady-state emission spectra are shown in FIG. 6.

Figure 7:
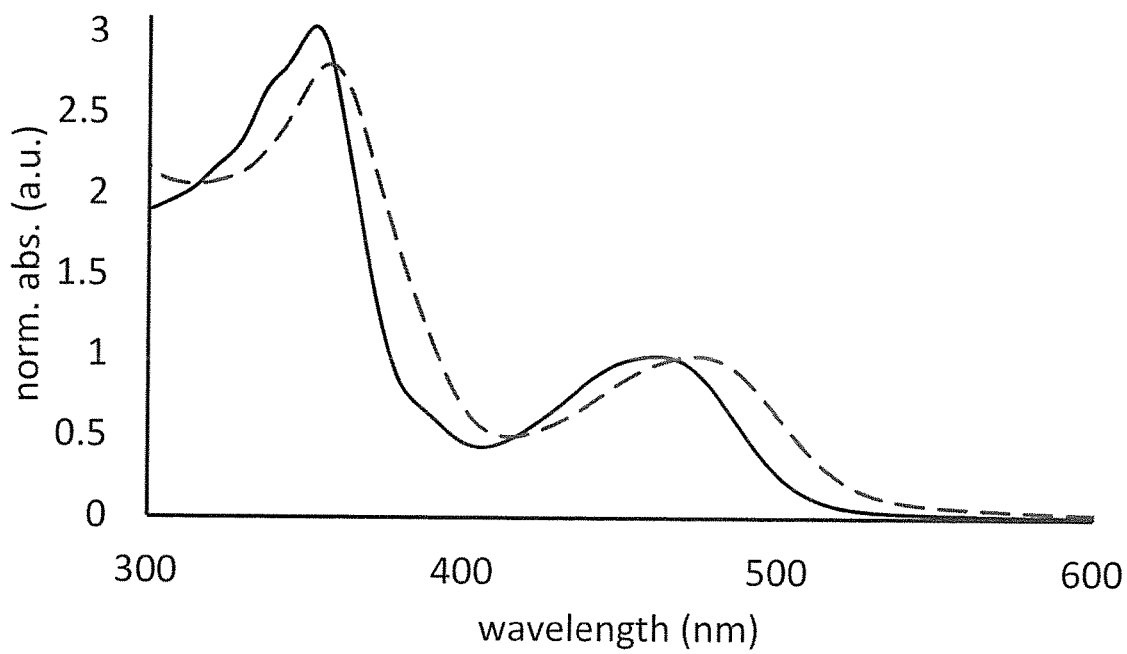
FIG. 7. UV-Vis absorption spectra of 1 (black solid line) and 2 (red dashed line) in $CH_2Cl_2$ ([ ]=100 μM, $N_2$-sat.).
Figure 8:
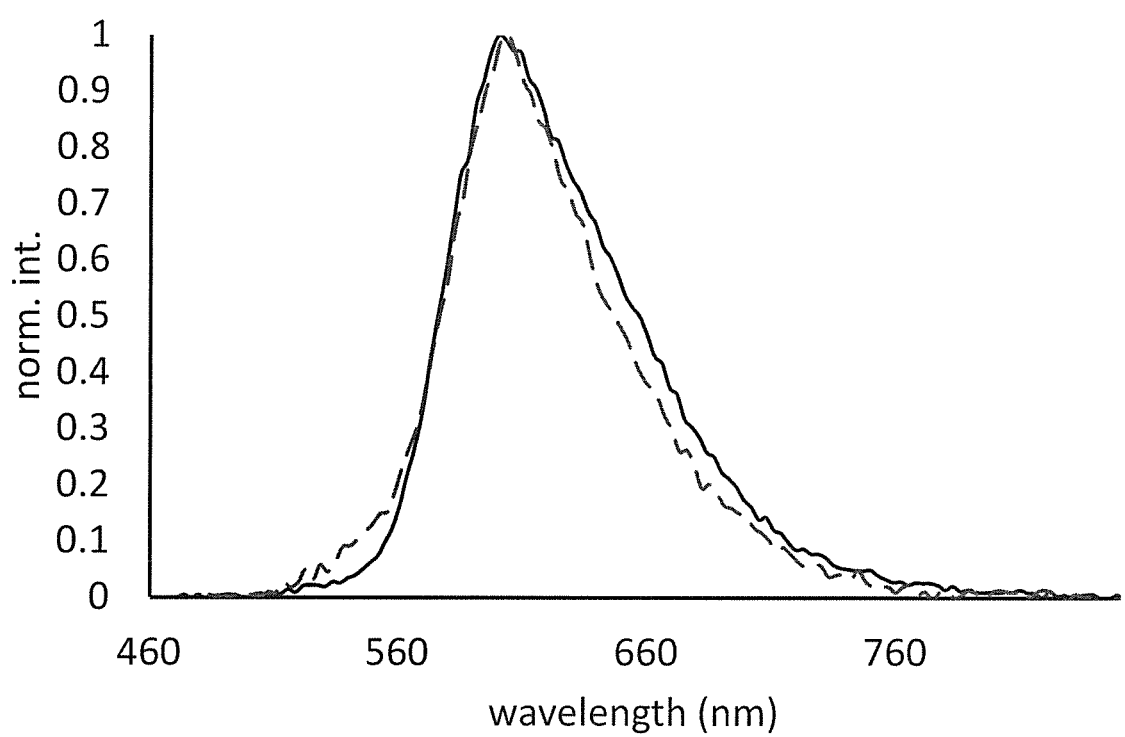
FIG. 8. Normalized emission spectra of 1 (solid, black line) and 2 (dashed, red line) in $CH_2Cl_2$ ([ ]=100 μM, $N_2$-saturated).
Figure 9:
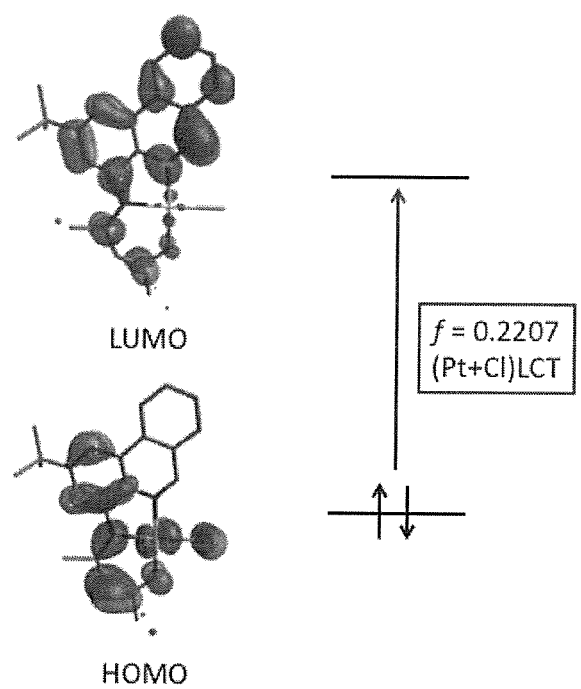
FIG. 9. TD-DFT analysis of lowest energy absorbance transition (1: absorbance calculated=442, experimental=461; 2: absorbance calculated=456, experimental=474).

In comparison, the platinum compounds 1 and 2 are orange-red compounds, and with a bathochromically shifted lowest energy absorption band assigned as (metal+halide)-to-ligand charge transfer. The charge-transfer nature of this absorption was corroborated by its hypsochromic shift in increasingly polar solvents, corresponding to negative solvatochromism. Time-dependent density functional theory (TD-DFT) calculations further support this assignment. Compounds 1 and 2 are also emissive in solution. The quantum yields of photoluminescence are oxygen sensitive. The emission is therefore attributable to phosphorescence from a triplet excited state, with fast intersystem crossing owing to the presence of the heavy element platinum (24). The wavelength of photoluminescence is significantly redshifted from fluorescence from the proligands and relatively strong (high quantum yields) for red platinum emitters. A representative spectrum is shown in FIG. 7. The oxygen sensitivity of the emission makes the hypoxic environment of certain cancer cells a viable target for observing emission (36). The photophysical properties of both proligands and platinum complexes are summarized in Table 3.

To assess the biological activities of 'in-plane' phenanthridine-containing monofunctional Pt(II) compounds, in vitro cytotoxicities were evaluated using MTT (MTT=[3-(4,5-dimethylthiazol-2-yl)-2,5-diphenyltetrazolium bromide] assays in two different cancer cell lines, discussed below. The results revealed promising activity, as well as a dependence on substituent structure. For example, 2 ($R=CF_3$) showed much higher in vitro efficacy as compared to cisplatin, as well as less resistance than cisplatin ($IC_{50}$ of A2780cis/IC50 of A2780) against both A2780 (cisplatin sensitive) and A2780cis (cisplatin resistant) ovarian cancer cell lines. In addition, neither the 4-aminophenanthridine precursors nor the proligands L1 or L2 themselves are effective in the absence of platinum(II). As noted above, intercalation enhances covalent binding and ultimately boosts the number of complex-DNA adducts observed for phenanthriplatin, but only when these two processes are simultaneous (30). Phenanthridines in general are anticipated to interact with DNA via an intercalation mechanism, similar to the mechanism of operation of the DNA stain ethidium bromide, of which phenanthridine forms the molecular core (19). The lack of activity in the absence of platinum(II) highlights the key role for the metal centre in the cytotoxicity. The differing profile compared to cisplatin (i.e., higher in vitro efficacy and lower cross-resistance) implies a different mechanism of operation from cisplatin, which, considering to the planar structure of 1 and 2 compared to phenanthriplatin (10) likely involves some degree of intercalation. The higher efficacy for 2 ($R=CF_3$) vs 1 (R=tBu) highlights the opportunity to fine-tune biological activity via ligand backbone substitution.

Figure 2:
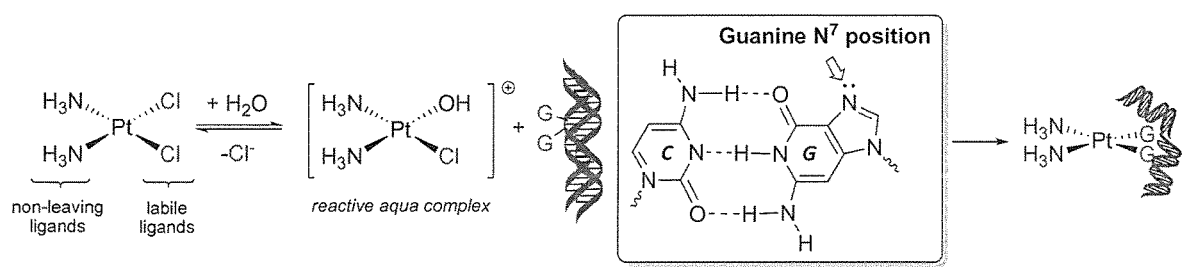
FIG. 2. Aquation of cisplatin and schematic mechanism of DNA binding, where G represents a guanine nucleobase.
Figure 14:
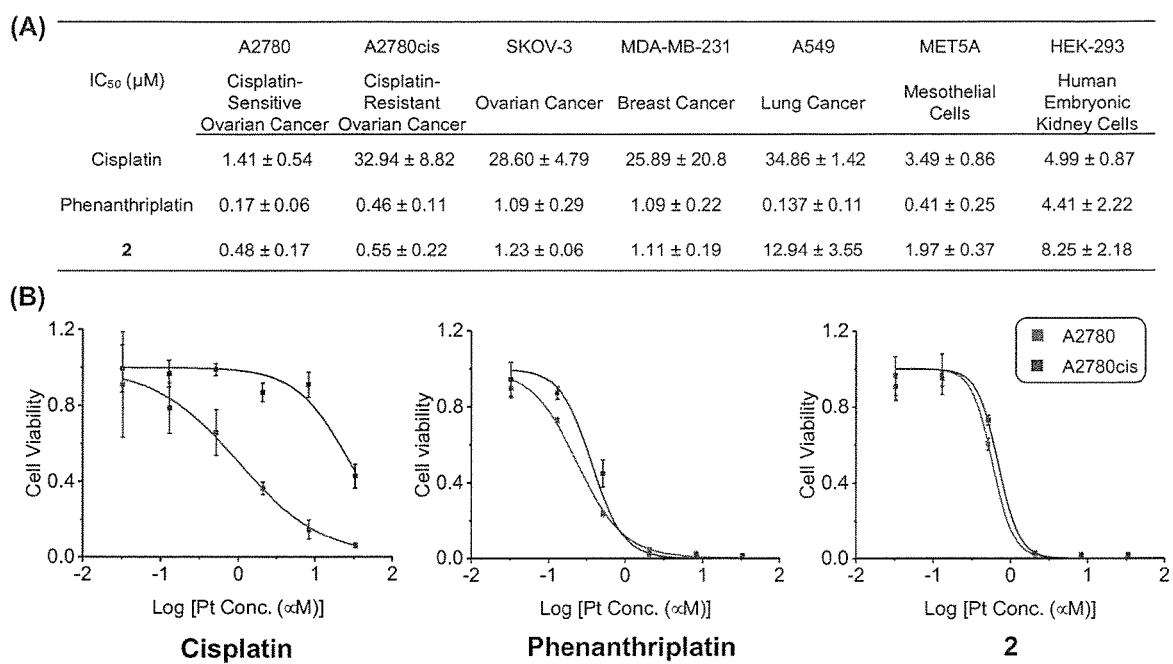
FIG. 14. Cytotoxicity profiles of cisplatin, phenthriplatin, and 2 against a panel of human cancer and normal cell lines: (A) table of $IC_{50}$ values, and (B) killing curves of cisplatin, phenanthriplatin, and 2 against A2780 and A2780cis ovarian cancer cells highlighting the lower resistance factor (RF) of 2.

With these results in hand, complex 2 was selected for further screening against additional human cancer and non-cancerous cell lines, including the non-small cell lung cancer cell line A549, ovarian cancer cell line A2780, and cisplatin-resistant ovarian cancer cell line A2780cis, ovarian cancer cell line SKOV-3, triple-negative breast cancer cell line MDA-MB-231, non-cancerous mesothelial cell line MET-5A, and non-cancerous kidney cell line HEK293. Cisplatin and phenanthriplatin were used as controls. Cancer and normal cells were treated for 72 h and cell viability was assessed. The $IC_{50}$ values represent compound concentrations required to inhibit cell growth by 50%, and these data tabulated in FIG. 14A. Compared to cisplatin, 2 exhibits much lower $IC_{50}$ values among all tested cell lines. For example, in A2780cis cisplatin-resistant ovarian cancer cell line (FIG. 14A), $IC_{50}$ (2)=0.55±0.22 µM is 58 times lower than that of cisplatin ($IC_{50}$=32.94±8.82 µM). Across the tested cancer cell lines, 2 has comparable efficacy to phenanthriplatin under the conditions tested. On the other hand, 2 proved less toxic than phenanthriplatin against normal cells (MET-5A and HEK293). Notably, as shown in FIG. 14B, 2 displays a lower resistance factor (RF= $IC_{50(A2780cis)}/IC_{50(A2780)}$=1.1) in the ovarian cancer cell lines than cisplatin (RF=23) or phenanthriplatin (RF=2.7). The MTT results collectively support that the newly developed platinum compound 2 shows a superior therapeutic index as compared to cisplatin and phenanthriplatin in vitro.

Figure 15:
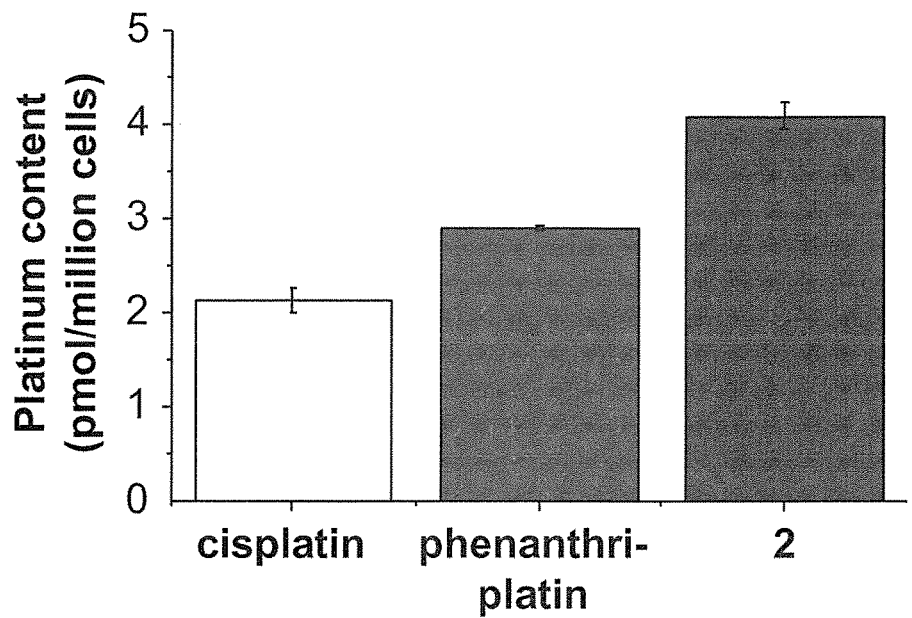
FIG. 15. Cellular uptake of cisplatin, phenthriplatin, and 2 in SKOV3 ovarian cancer cells ([Pt]=2 µM, 24 h at 37° C., 5% $CO_2$).
Figure 16:
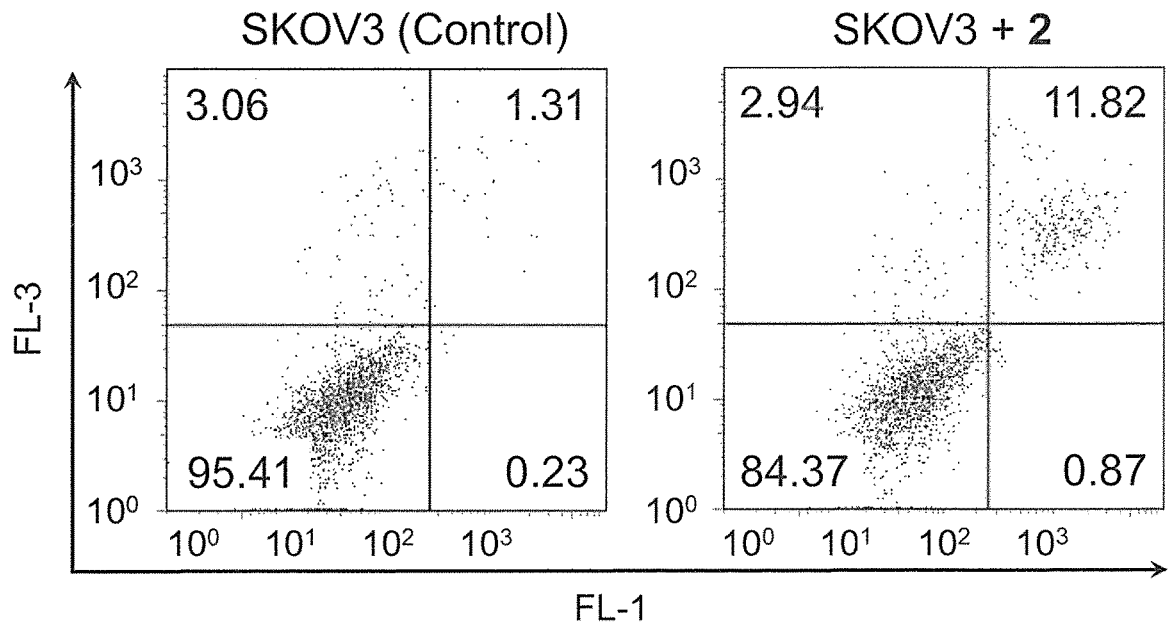
FIG. 16. Annexin V/PI flow cytometric analysis of the apopotic events of SKOV3 cells with or without the treatment of 2 ([Pt]=1 µM, 72 h at 37° C., 5% $CO_2$).

We next investigated the cellular uptake and cellular responses of 2 in order to better understand its cellular behavior. First, cellular uptake was evaluated using graphite furnace atomic absorption spectroscopy (GFAAS), with cisplatin and phenanthriplatin again employed as controls. In the experiment, SKOV3 cells were incubated with the different platinum compounds (2 µM) for 24 h. The treated cells were then harvested and digested for GFAAS analysis. Complex 2 exhibits higher cellular uptake (4.09±0.138 pmol Pt per million cells) compared with cisplatin (2.12±0.129 pmol Pt per million cells) or phenthriplatin (2.88±0.023 pmol Pt per million cells; FIG. 15).

As will be apparent to one of skill in the art, any suitable oxidizing compound may be used within the invention, for example, any suitable oxidizing compound known to work with cisplatin.

According to another aspect of the invention, there is provided a method of treating cancer comprising administering to an individual in need of such treatment an effective amount of an anti-cancer drug comprising a compound of formula (I) or a compound of formula (I).

As will be known to those of skill in the art, platinum-based drugs such as cisplatin and oxaliplatin have been used alone or in combination with another known anti-cancer drug, for example, fluorouracil, etoposide, paclitaxel, leucovorin, capecitabine and the like to treat a variety of cancers including but by no means limited to anal cancer, bladder cancer, cervical cancer, esophageal cancer, gastric cancer, head and neck cancer, non-small cell lung cancer, small cell lung cancer, ovarian cancer, prostate cancer, testicular cancer, thymic cancer, neuroendocrine cancer, soft tissue sarcoma, breast cancer, endometrial cancer, thyroid cancer, melanoma and colorectal cancer.

Accordingly, an individual in need of such treatment is an individual who has been diagnosed with a cancer, for example, one of the cancers listed above.

As discussed herein, the compounds of the invention have been shown to be effective against ovarian cancer cell lines that are cisplatin-sensitive and cisplatin-resistant. Accordingly, it is maintained that it is a sound prediction that these compounds will be effective against at least the same types of cancer as the other platinum-based drugs. It is maintained that this is particularly true in view of the mechanism of action of the compounds, as discussed herein.

As will be known by those of skill in the art, for maximum effectiveness, cisplatin and other known platinum-based drugs must be delivered to the tumor site. Accordingly, there are a variety of means known for delivery of cisplatin, including but by no means limited to polymer-based delivery systems, solid lipid-based delivery systems and inorganic nanoparticle-based delivery systems. Given that the compounds of the invention are also platinum-based drugs, it is expected that these compounds will also be amenable to enhanced delivery using the established drug-delivery approaches possible for cisplatin and related compounds.

As will be apparent to one of skill in the art, "an effective amount" may be determined through routine experimentation. Factors that may influence an "effective amount" include but are by no means limited to the age, weight and general condition of the individual as well as the type of cancer as well as the severity thereof. For illustrative purposes, an effective amount may be from about 1 nM to 100 µM.

As will be appreciated by one of skill in the art, administration of an effective amount of one of the compounds of the invention will accomplish at least one of the following: reduction of tumor size or reduction of tumor mass.

According to another aspect of the invention, there is use of an anti-cancer drug or compound comprising or consisting of or consisting essentially of a compound of formula (I) or a compound of formula (I) to treat cancer.

As will be appreciated by one of skill in the art, the compounds of the invention may be used to treat any unwanted cell growth in an individual.

The invention will now be further elucidated and explained by way of examples. However, the invention is not necessarily limited to the examples.

Example 1—Synthesis 4-amino substituted phenanthridines (2-R) suitable for chemical elaboration were isolated following the synthetic procedure outlined in Scheme 1. Selection of appropriate substituents (R groups in the 2-position) is anticipated to be critical for two reasons: one, their influence on emission wavelength/quantum yield of emission (and other photophysical properties) as a result of the substituent's electron-donating/electron-withdrawing/electron-neutral nature; and two, the potential influence on bioavailability and bioactivity due to both sterics and electronics. For example, selective fluorine substitution, isosteric to hydrogen, has been demonstrated to greatly influence the biochemical uptake and behaviour of substituted natural products and organic drugs (21), while additionally providing a convenient $^{19}F$ NMR handle. Such substituted phenanthridines are easier to access synthetically than unsubstituted variants (R═H), as the corresponding iodoanilines can be more readily prepared and are reactive in the tandem Pd-catalyzed cross-coupling/condensation reaction used to construct the fused tricyclic ring system of 1-R (Scheme 1a) (17). Reduction of the nitro group with $Zn/NH_2$—$NH_2$ and formic acid gives the 4-amino substituted phenanthridines 2-R in good to high yields (Scheme 1b).

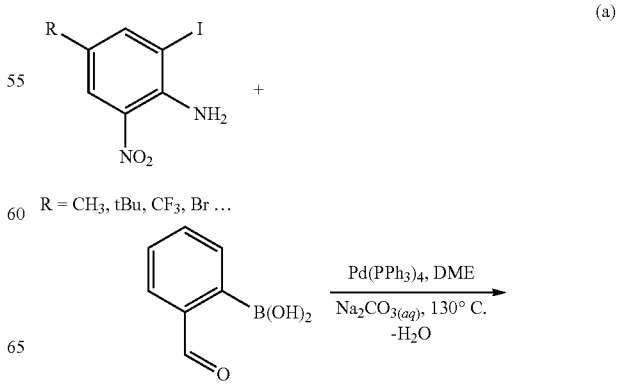

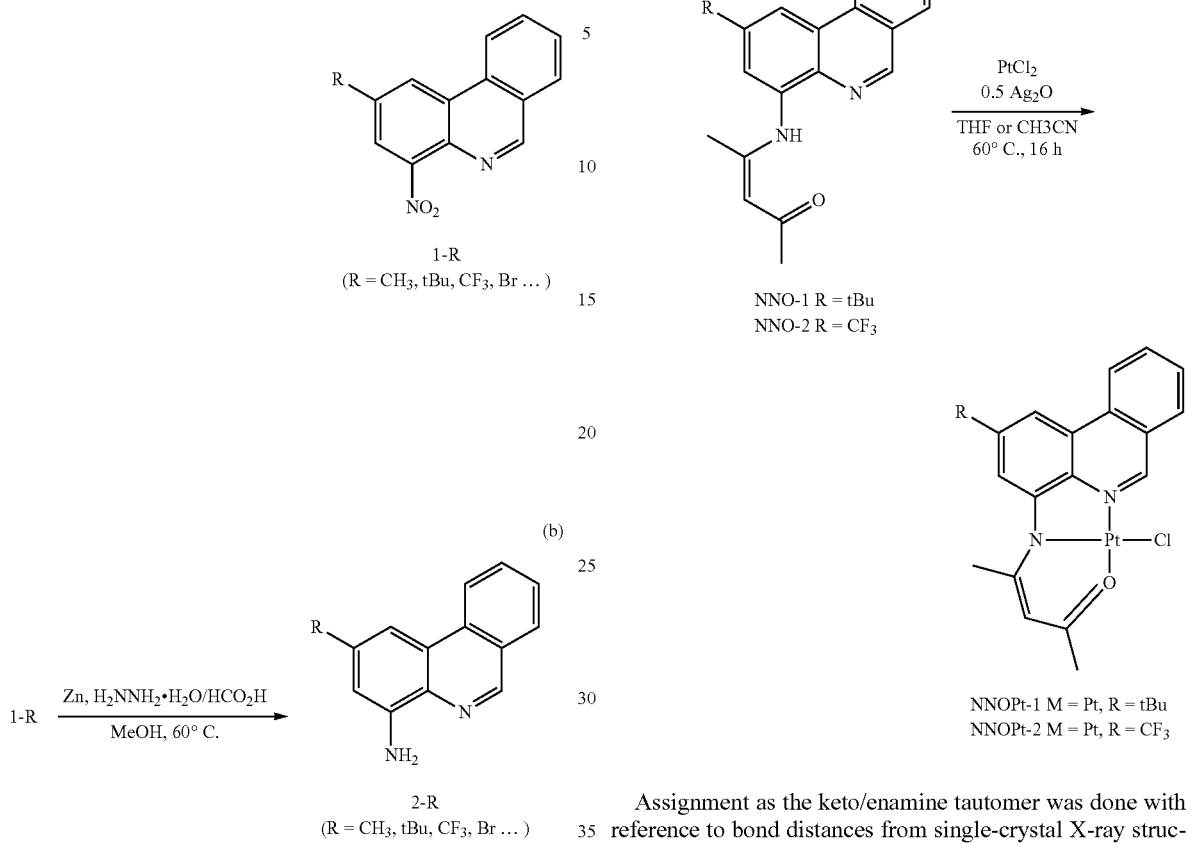

Scheme 1. Preparation of 4-Aminophenanthridine Precursors.

This synthetic protocol is furthermore amenable to a broad range of chemical functionalization, including the installation of amide units or phosphate units for attachment of antibodies or other targeting groups as described above. Proligand synthesis is exemplified through the preparation of NNO1-2 (Scheme 2), wherein acid-catalyzed condensation in the presence of excess acetylacetone was used to yield the desired proligands in respectable yields.

Assignment as the keto/enamine tautomer was done with reference to bond distances from single-crystal X-ray structures of the proligand L1 (FIG. 3), as well by comparing the appropriate NMR and IR parameters with related literature compounds (22).

Following synthesis and isolation of the phenanthridine-containing ligands, metalation with divalent platinum was carried out in the presence of 0.5 molar equivalents of silver(I) oxide. Silver(I) oxide serves both as base and halide abstracting reagent, to effect formal removal of HCl upon binding to platinum. Alternative preparations using oxygenous or nitrogenous Brönsted bases also work (e.g., $NEt_3$ or NaOtBu). We were accordingly able to isolate NNOPt compounds in good yields. Single-crystal X-ray diffraction (FIG. 4) corroborated solution phase structural assignments with solid-state data. Thus the "in-plane" nature of the phenanthridine unit in our novel monofunctional drug candidates has been verified.

Similar to phenanthriplatin (FIG. 1), three of four coordination sites are taken up by non-labile ligands, with only a single chloride available for displacement by DNA nucleobases. This ensures "monofunctional" behaviour towards DNA.

Example 2—Electronic Absorption and Photoluminescence

The proligands L1 and L2 are both bright yellow, crystalline solids, and give yellow solutions, with a broad absorption just at the edge of the visible range (FIG. 5). The proligands are weakly emissive in solution, with representative emission spectra shown in FIG. 6. Emission data has been collected using steady-state fluorimetry conditions.

In comparison, the platinum compounds 1 and 2 are red in the solid state, and give rise to a red-shifted absorption band assigned as (metal+halide)-to-ligand charge transfer, corroborated by solvatochromism of the lowest energy absorption and time-dependent density functional theory (TD-DFT) calculations. Emission is oxygen-sensitive and therefore attributed to phosphorescence from a triplet state excited state, facilitated by fast intersystem crossing thanks to spin-orbit coupling with the heavy element platinum (24). Emission is significantly red-shifted from fluorescence from the proligands, which are only weakly emissive ($\lambda_{em}$=460 nm; Table 1), and quite strong (high quantum yields) for platinum emitters. A representative spectrum is shown in FIG. 7. The oxygen sensitivity of the emission makes the hypoxic environment of certain cancer cells a viable target for observing emission. The photophysical properties of both proligands and platinum complexes are summarized in Table 1. Both 1 and 2 emit in the yellow-orange region of the electromagnetic spectrum (~600 nm), with respectably high quantum yields (approaching 21% for 2) (24). High quantum yields, which measure the ratio of photons of light absorbed to photons of light re-emitted, is critical for achieving high resolution in emission imaging (41).

Example 3—In-Vitro C Assays

To assess the biological activities of our 'in-plane' phenanthridine-containing monofunctional Pt(II) compounds, in vitro cytotoxicities were evaluated using MTT (MTT=[3-(4,5-dimethylthiazol-2-yl)-2,5-diphenyltetrazolium bromide] assays in two different cancer cell lines (see materials and methods). Table 2 reports IC$_{50}$ (50% growth inhibition concentrations) for two separate ovarian cancer cell lines. The results reveal promising activity, as well as a dependence on substituent structure. For example, 2 shows much higher in vitro efficacy as compared to cisplatin, as well as less resistance than cisplatin (IC50 of A2780cis/IC50 of A2780) against both A2780 (cisplatin sensitive) and A2780cis (cisplatin resistant) ovarian cancer cell lines. In addition, neither the phenanthridinyl amines (2-R) nor the ligand itself (L2) are effective in the absence of platinum(II). While not wishing to be bound or limited to a particular theory or hypothesis, it is believed that substituted phenanthridines interact with DNA via an intercalation mechanism, similar to the mechanism of operation of the DNA stain ethidium bromide (19). The lack of activity in the absence of platinum(II) highlights the key role for the metal centre in the cytotoxicity. The differing profile compared to cisplatin (i.e., higher in vitro efficacy and lower cross-resistance) implies a different mechanism of operation from cisplatin, which, considering to the planar structure of NNOPt compared to phenanthriplatin (10) likely involves some degree of intercalation. The higher efficacy for 2 (R=CF$_3$) vs 1 (R=tBu) highlights the opportunity to fine-tune biological activity via ligand backbone substitution.

Example 4—Synthesis of Proligands and Metal Complexes

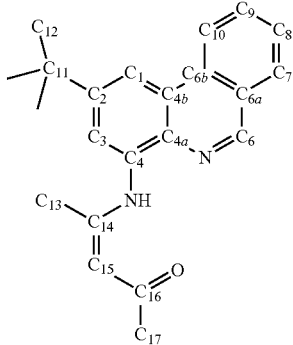

Synthesis of 4-(2'-tert-butyl-4-aminophenanthridinyl)-3-penten-2-one (L1): A Teflon-stoppered flask was charged with 2-tert-butyl-4-aminophenanthridine (1.01 g, 3.03 mmol), acetylacetone (1.3 mL, 12.7 mmol), p-tosic acid (0.05 g, 0.27 mmol), toluene (10 mL) and 4 Å molecular sieves. The reaction was then refluxed for 48 h after which the reaction mixture was filtered over Celite. The solvent was then evaporated to isolate an oily dark brown residue, which was dissolved in CH$_2$Cl$_2$ and passed through a silica plug. The solvent was evaporated to isolate a beige, solid compound (0.858 g, 64% yield). $^1$H NMR (CDCl$_3$, 300 MHz, 22° C.): δ 13.44 (s, 1H; NH), 9.31 (s, 1H; C$_6$—H), 8.63 (d, J$_{HH}$=8.3 Hz, 1H; C$_{10}$—H), 8.32 (d, J$_{HH}$=1.9 Hz, 1H; C$_1$—H), 8.06 (d, J$_{HH}$=7.3 Hz, 1H; C$_7$—H), 7.86 (ddd, J$_{HH}$=1.3 Hz, 7.7 Hz, 8.5 Hz, 1H; C$_8$—H), 7.71 (ddd overlapped, J$_{HH}$=0.9 Hz, 7.5 Hz, 8.5 Hz, 1H; C$_9$—H), 7.60 (d, J$_{HH}$=1.9 Hz, 1H; C$_3$—H), 5.35 (s, 1H; C$_{15}$—H), 2.23 (s, 3H; C$_{13}$—H), 2.18 (s, 3H; C$_{17}$—H), 1.49 ppm (s, 9H; C$_{12}$—H). $^{13}$C{$^1$H} NMR (CDCl$_3$, 75 MHz, 22° C.): δ 196.33 (C$_{16}$), 158.65 (C$_{14}$), 152.42 (C$_6$), 149.74 (C$_2$), 136.91 (C$_4$), 136.12 (C$_{4a}$), 132.74 (C$_{4b}$), 130.97 (C$_8$), 129.06 (C$_7$), 127.65 (C$_9$), 126.83 (C$_{6a}$), 124.39 (C$_{6b}$), 122.16 (C$_{10}$), 119.68 (C$_3$), 113.88 (C$_1$), 99.74 (C$_{15}$), 35.46 (C$_{11}$), 31.57 (C$_{12}$), 29.54 (C$_{17}$), 21.09 ppm (C$_{13}$). IR (ATR; ν (cm$^{-1}$)): 3100-2800 (C—H stretch, b, w), 1617 (C=O stretch, n, m), 1570 (N—H wag, n, s).

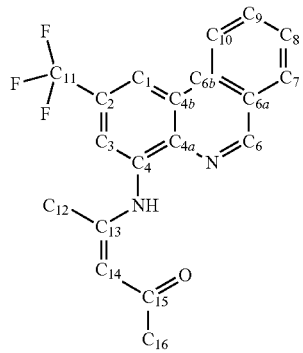

Synthesis of 4-(2'-trifluoromethyl-4'-aminophenanthridinyl)-3-penten-2-one (L2): A Teflon-stoppered flask was charged with 2-trifluoromethyl-4-aminophenanthridine (1.09 g, 3.15 mmol), acetylacetone (1.3 mL, 12.7 mmol), p-tosic acid (0.04 g, 0.23 mmol), toluene (10 mL), and 4 Å molecular sieves. The reaction was then refluxed for 48 h after which the reaction mixture was filtered over celite. The solvent was then evaporated to isolate an oily dark brown residue, which was dissolved in $CH_2Cl_2$ and passed through a silica plug. The solvent was evaporated to isolate an off-white, solid compound (0.911 g, 64% yield). $^1H$ NMR ($CDCl_3$, 300 MHz, 22° C.): δ 13.72 (s, 1H; NH), 9.44 (s, 1H; $C_6$—H), 8.60 (d, $J_{HH}$=8.3 Hz, 1H; $C_{10}$—H), 8.49 (s, 1H; $C_1$—H), 8.12 (d, $J_{HH}$=7.9H, 1H; $C_7$—H), 7.93 (ddd, $J_{HH}$=1.2 Hz, 7.7 Hz, 8.7 Hz, 1H; $C_8$—H), 7.79 (ddd overlapped, $J_{HH}$=0.8 Hz, 7.5 Hz, 8.7 Hz, 1H; $C_9$—H), 7.68 (d, $J_{HH}$=1.4 Hz, 1H; $C_3$—H), 5.41 (s, 1H; $C_{14}$—H), 2.36 (s, 3H; $C_{12}$—H), 2.21 ppm (s, 3H; $C_{16}$—H). $^{13}C\{^1H\}$ NMR ($CDCl_3$, 75 MHz, 22° C.): δ 197.22 ($C_{15}$), 156.59 ($C_{13}$), 154.58 ($C_6$), 138.73 ($C_4$), 137.90 ($C_2$), 132.34 ($C_{6a}$), 131.90 ($C_8$), 129.32 ($C_7$), 128.73 ($C_9$), 126.91 ($C_{6b}$), 124.71 ($C_{4a}$), 122.47 ($C_{4b}$), 122.34 ($C_{10}$), 114.08 (q overlapped, $C_1$), 113.94 (q overlapped, $C_3$), 101.79 ($C_{14}$), 29.84 ($C_{16}$), 21.59 ppm ($C_{12}$), $C_{11}$—not observed. $^{19}F$ NMR ($CDCl_3$, 470 MHz, 22° C.): δ −62.25 ppm. IR (ATR; ν ($cm^{-1}$)): 3100-2800 (C—H stretch, b, w), 1634 (C═O stretch, n, s), 1579 (N—H wag, n, s).

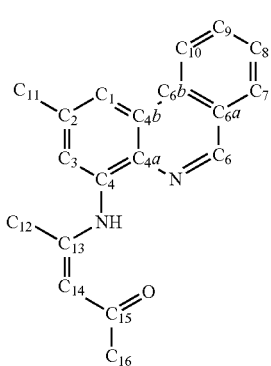

Synthesis of 4-(2'-methyl-4'-aminophenanthridinyl)-3-penten-2-one (L3): A Teflon-stoppered flask was charged with 2-methyl-4-aminophenanthridine[18] (1.00 g, 4.80 mmol), acetylacetone (1.50 mL, 14.6 mmol), p-tosic acid (45.9 mg, 0.241 mmol), toluene (10 mL) and 4 Å molecular sieves. The mixture was heated to reflux for 48 h, then cooled and filtered over Celite. The solvent was evaporated to leave an oily dark brown residue, which was triturated diisopropyl ether to leave a light brown solid (1.00 g, 72% yield). $^1H$ NMR ($CDCl_3$, 300 MHz, 22° C.): δ 13.53 (br s, 1H; N—H), 9.29 (s, 1H; $C_6$—H), 8.55 (d, $J_{HH}$=8.2 Hz, 1H; $C_{10}$—H), 8.06 (s, 1H; $C_1$—H), 8.04 (dd, $^3J_{HH}$=8.1 Hz, $^4J_{HH}$=0.6 Hz, 1H; $C_7$—H), 7.83 (m, 1H; $C_8$—H), 7.69 (m, 1H; $C_9$—H), 7.34 (d, $^4J_{HH}$=1.1 Hz, 1H; $C_{16}$—H), 5.33 (s, 1H; $C_{14}$—H), 2.59 (s, 3H; $C_{11}$—H), 2.26 (s, 3H; $C_{12}$—H), 2.18 ppm (s, 3H, $C_{16}$—H). $^{13}C\{^1H\}$ NMR ($CDCl_3$, 75 MHz, 22° C.): 196.38 ($C_{15}$), 158.20 ($C_{13}$), 151.92 ($C_6$), 137.19 ($C_4$), 136.66 ($C_{4a}$), 135.67 ($C_2$), 132.16 ($C_{4b}$), 130.93 ($C_9$), 128.93 ($C_7$), 127.70 ($C_8$), 126.76 ($C_{6a}$), 124.80 ($C_{6b}$), 122.23 ($C_{10}$), 121.58 ($C_3$), 117.46 ($C_1$), 100.10 ($C_{14}$), 29.57 ($C_{16}$), 22.56 ($C_{11}$), 21.36 ppm ($C_{12}$).

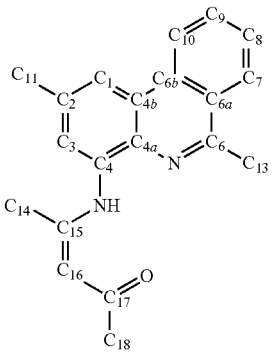

Synthesis of 4-(2',6'-dimethyl-4'-aminophenanthridinyl)-3-penten-2-one (L4): A Teflon-stoppered flask was charged with 2,6-dimethyl-4-aminophenanthridine (1.00 g, 4.51 mmol), acetylacetone (1.40 mL, 13.6 mmol), p-tosic acid (47.0 mg, 0.247 mmol), toluene (10 mL) and 4 Å molecular sieves. The mixture was refluxed for 48 h then cooled and filtered over Celite. The solvent was evaporated to leave an oily dark brown residue, which was triturated with diisopropyl ether to give a light brown solid (0.929 g, 68% yield). $^1H$ NMR ($CDCl_3$, 300 MHz, 22° C.): δ 13.61 (br s, 1H; N—H), 8.58 (d, $^3J_{HH}$=8.2 Hz, 1H; $C_{10}$—H), 8.21 (dd, $^3J_{HH}$=8.3 Hz, $^4J_{HH}$=0.8 Hz, 1H; $C_7$—H), 8.01 (s, 1H; $C_1$—H), 7.81 (m, 1H; $C_9$—H), 7.69 (m, 1H; $C_8$—H), 7.33 (d, $^4J_{HH}$=1.1 Hz, 1H; $C_3$—H), 5.32 (s, 1H; $C_{16}$—H), 3.12 (s, 3H; $C_{13}$—H), 2.60 (s, 3H; $C_{11}$—H), 2.35 (s, 3H; $C_{14}$—H), 2.21 ppm (s, 3H; $C_{18}$—H).

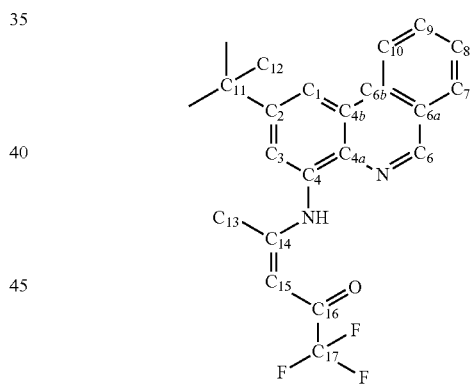

Synthesis of 1,1,1-trifluoromethyl-4-(2'-tert-butyl-4'-aminophenanthridinyl)-3-penten-2-one (L5): A Teflon-stoppered flask was charged with 2-tert-butyl-4-aminophenanthridine[25] (1.01 g, 4.04 mmol), 1,1,1-trifluoromethyl-2,4-pentanedione (1.50 mL, 12.4 mmol), p-tosic acid (42.7 mg, 0.224 mmol), toluene (10 mL) and 4 Å molecular sieves. The mixture was refluxed for 48 h then cooled and filtered over Celite. The solvent was evaporated to leave an oily dark brown residue, which was triturated diisopropyl ether to give a light brown solid (0.965 g, 64% yield). $^1H$ NMR ($CDCl_3$, 300 MHz, 22° C.): δ 13.46 (br s, 1H; N—H), 9.31 (s; $C_6$—H), 8.65 (d, $^3J_{HH}$=8.2 Hz, 1H; $C_7$—H), 8.47 (d, $^4J_{HH}$=1.9 HZ, 1H; $C_1$—H), 8.08 (dd, $^3J_{HH}$=7.9 Hz, $^4J_{HH}$=0.8 Hz, 1H; $C_5$—H), 7.91 (ddd, $^3J_{HH}$=9.1 Hz, $^3J_{HH}$=7.0 Hz, $^4J_{HH}$=0.9 Hz, 1H; $C_8$—H), 7.75 (ddd, $^3J_{HH}$=8.2 Hz, $^3J_{HH}$=6.9 Hz, $^4J_{HH}$=1.0 Hz, 1H; $C_9$—H), 7.66 (d, $^4J_{HH}$=1.6 Hz, 1H; $C_3$—H), 5.68 (s, 3H; $C_{14}$—H), 2.31 (s, 3H; $C_{13}$—H), 1.50 ppm (s, 9H; $C_{12}$—H). $^{13}C\{^1H\}$ NMR (CDCl$_3$, 75 MHz, 22° C.): 176.70 (q, $^2J_{FC}$=33.0 Hz; $C_{16}$), 166.76 ($C_{14}$), 153.17 ($C_6$), 149.88 ($C_2$), 136.32 ($C_4$), 135.02 ($C_{4b}$), 132.38 ($C_{6b}$), 129.23 ($C_7$), 128.09 ($C_9$), 126.80 ($C_{4a}$), 124.64 ($C_{6a}$), 122.15 ($C_{10}$), 121.32 ($C_3$), 116.35 ($C_1$), 92.44 ($C_{15}$), 35.54 ($C_{11}$), 31.52 ($C_{12}$), 21.50 ppm ($C_{13}$). $^{19}F$ NMR (CDCl$_3$, 282 MHz, 22° C.): −76.47 ppm (3F; $C_{17}$—F).

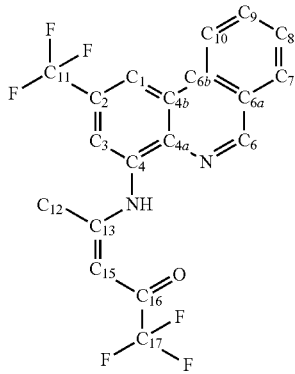

Synthesis of 1,1,1-trifluoromethyl-4-(2'-trifluoromethyl-4'-aminophenanthridinyl)-3-penten-2-one (L6): A Teflon-stoppered flask was charged with 2-trifluoromethyl-4-aminophenanthridine (1.00 g, 3.84 mmol), 1,1,1-trifluoromethyl-2,4-pentanedione (1.50 mL, 12.4 mmol), p-tosic acid (40.0 mg, 0.210 mmol), toluene (10 mL) and 4 Å molecular sieves. The mixture was refluxed for 48 h then cooled and filtered over Celite. The solvent was evaporated to leave an oily dark brown residue, which was triturated diisopropyl ether to give a light brown solid (1.02 g, 67% yield). $^1H$ NMR (CDCl$_3$, 300 MHz, 22° C.): δ 13.69 (br s, 1H; N—H), 9.46 (s, 1H; $C_6$—H), 8.67 (s, 1H; $C_1$—H), 8.65 (d, $^3J_{HH}$=8.3 Hz, 1H; $C_{10}$—H), 8.17 (d, $^3J_{HH}$=7.7 Hz, 1H; $C_7$—H), 7.99 (m, 1H; $C_8$—H), 7.85 (m, 1H; $C_9$—H), 7.78 (s, 1H; $C_3$—H), 5.73 (s, 1H; $C_{15}$—H), 2.46 ppm (s, 3H; $C_{12}$—H). $^{13}C\{^1H\}$ NMR (CDCl$_3$, 75 MHz, 22° C.): 165.05 ($C_{13}$), 155.50 ($C_6$), 138.45 ($C_2$), 136.80 ($C_4$), 132.38 ($C_8$), 132.09 ($C_{4b}$), 129.56 ($C_7$), 129.23 ($C_9$), 126.95 ($C_{6b}$), 125.01 ($C_{4a}$), 122.35 ($C_{10}$), 116.98 (q, $^3J_{FC}$=4.0 Hz; $C_1$), 116.35 (q, $^3J_{FC}$=3.2 Hz; $C_3$), 93.98 ($C_{15}$), 21.95 ppm ($C_{12}$). $^{19}F$ NMR (CDCl$_3$, 282 MHz, 22° C.): −62.14 (3F, $C_{11}$—F), −76.47 ppm (3F, $C_{17}$—F).

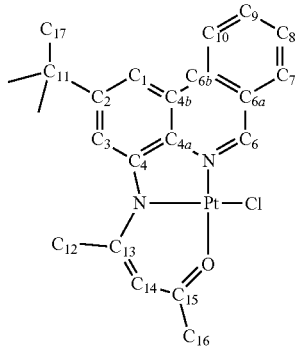

Synthesis of [Pt(tBu-phenanthridine-nacac)Cl] (1): A solution of L1 (0.501 g, 1.51 mmol) in THF (25 mL) was added to a suspension of PtCl$_2$ (407 mg, 1.53 mmol), Ag$_2$O (179 mg, 0.774 mmol) and 4 Å molecular sieves in THF (25 mL). The mixture was protected from light and refluxed at 60° C. for 16 h. The mixture was then filtered over Celite then the solvent was evaporated in vacuo to isolate an orange solid compound. The residue was then recrystallized via vapour diffusion of Et$_2$O in CHCl$_3$ (739 mg, 87% yield). $^1H$ NMR (CDCl$_3$, 500 MHz, 22° C.): δ 10.03 (s, 1H, $^3J_{PtH}$=39 Hz; $C_{6a}$—H), 8.57 (d, $J_{HH}$=8.3 Hz, 1H; $C_{10}$—H), 8.10 (d, $J_{HH}$=1.2 Hz, 1H; $C_1$—H), 8.07 (d, $J_{HH}$=7.9 Hz, 1H; $C_7$—H), 7.99 (ddd, $J_{HH}$=7.5H, 9 Hz, 1H; $C_8$—H), 7.78 (d, $J_{HH}$=1.3 Hz, 1H; $C_3$—H), 7.74 (ddd, $J_{HH}$=7.5 Hz, 8.5 Hz, 1H; $C_9$—H), 5.32 (s, 1H; $C_{14}$—H), 2.46 (s, 3H; $C_{12}$—H), 2.07 (s, 3H; $C_{16}$—H), 1.50 ppm (s, 9H; $C_{17}$—H). $^{13}C\{^1H\}$ NMR (CDCl$_3$, 125 MHz, 22° C.): 179.80 ($C_{15}$), 157.85 ($C_{13}$), 155.01 ($C_6$), 151.96 ($C_2$), 148.78 ($C_4$), 139.22 ($C_{4a}$), 133.54 ($C_8$), 132.36 ($C_{6a}$), 130.18 ($C_7$), 128.83 ($C_9$), 126.38 ($C_{6b}$), 125.19 ($C_{4b}$), 122.48 ($C_{10}$), 119.57 ($C_3$), 114.02 ($C_1$), 106.66 ($C_{14}$), 35.72 ($C_{11}$), 31.61 ($C_{17}$), 25.98 ($C_{16}$), 25.66 ppm ($C_{12}$).

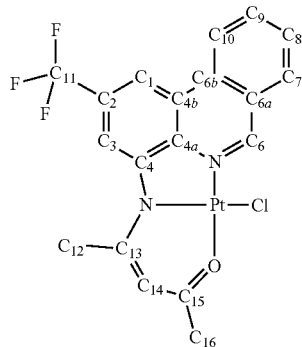

Synthesis of [Pt(CF$_3$-phenanthridinenacac)Cl] (2): A solution of L2 (501 mg, 1.46 mmol) in THF (25 mL) was added to a suspension of PtCl$_3$ (398 mg, 1.50 mmol), Ag$_2$O (174 mg, 0.752 mmol) and 4 Å molecular sieves in THF (25 mL). The mixture was protected from light and refluxed at 60° C. for 16 h. The mixture was then filtered over Celite then the solvent was evaporated in vacuo to isolate an orange solid compound. Dark red crystals were obtained by vapour diffusion of Et$_2$O in a solution of CHCl$_3$ (722 mg, 86% yield). $^1H$ NMR (CDCl$_3$, 500 MHz, 22° C.): δ 10.20 (s, 1H, $^3J_{PtH}$=39 Hz; $C_6$—H), 8.57 (d, $J_{HH}$=7.9 Hz, 1H; $C_{10}$—H), 8.33 (s, 1H; $C_1$—H), 8.18 (d, $J_{HH}$=7.6 Hz, 1H; $C_7$—H), 8.10 (ddd, $J_{HH}$=7.0H, 9.4 Hz, 1H; $C_8$—H), 7.88 (s overlapping, 1H; $C_3$—H), 7.87 (ddd overlapping, 1H; $C_9$—H), 5.39 (s, 1H; $C_{10}$—H), 2.46 (s, 3H; $C_{12}$—H), 2.09 ppm (s, 3H; $C_{16}$—H). $^{13}C\{^1H\}$ NMR (CDCl$_3$, 125 MHz, 22° C.): 6181.84 ($C_{15}$), 158.39 ($C_{13}$), 158.01 ($C_6$), 150.00 ($C_4$), 142.00 ($C_{6b}$), 134.70 ($C_8$), 132.10 ($C_{6a}$), 130.70 ($C_7$), 130.06 ($C_4$a), 126.49 ($C_2$), 125.78 ($C_9$), 124.74 ($C_{6b}$), 122.66 ($C_{4b}$), 122.57 ($C_{10}$), 116.40 (q, $J_{CF}$=3.6 Hz; $C_3$), 115.13 (q, $J_{CF}$=3.6 Hz; $C_{14}$), 107.63 ($C_{14}$), 25.98 ($C_{16}$), 25.96 ppm ($C_{12}$). $^{19}F$ NMR (CDCl$_3$, 470 MHz, 22° C.): δ −62.14 ppm.

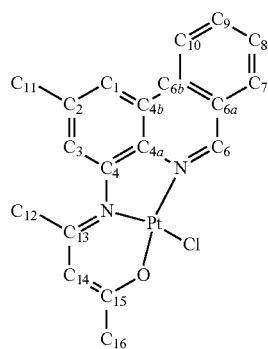

Synthesis of [Pt(CH$_3$-phenanthridinenacac)Cl] (3): A solution of L3 (200 mg, 0.690 mmol) in THF (25 mL) was added to a suspension of PtCl$_2$ (186 mg, 0.701 mmol), Ag$_2$O (81.2 mg, 0.350 mmol) and 4 Å molecular sieves in THF (10 mL). The mixture was protected from light and refluxed at 60° C. for 16 h. The mixture was then cooled and filtered over Celite. The solvent was next was evaporated in vacuo to leave an orange solid. The residue was triturated with diethylether to give a bright orange compound. $^1$H NMR (CDCl$_3$, 500 MHz, 22° C.): δ 10.04 (s, 1H, $^3J_{PtH}$=38.6 Hz; C$_6$—H), 8.51 (d, 1H; C$_{10}$—H), 8.09 (d, 1H; C$_7$—H), 7.98 (m, 1H; C$_9$—H), 7.87 (s, 1H; C$_1$—H), 7.75 (m, 1H; C$_8$—H), 7.55 (s, 1H; C$_3$—H), 5.30 (s, 1H; C$_{14}$—H), 2.64 (s, 3H; C$_{11}$—H), 2.44 (s, 3H; C$_{12}$—H), 2.08 ppm (s, 3H; C$_{13}$—H). $^{13}$C{$^1$H} NMR (CDCl$_3$, 125 MHz, 22° C.): δ 179.91 (C$_{16}$), 158.12 (C$_{13}$), 154.88 (C$_{10}$), 138.95, 135.93, 133.55 (C$_3$), 131.97, 130.13 (C$_7$), 129.19, 128.96 (C$_8$), 128.49, 122.57 (C$_{10}$), 122.51 (C$_3$), 117.93 (C$_1$), 106.76 (C$_{14}$), 26.14 (C$_{12}$), 25.71 (C$_{16}$), 22.65 ppm (C$_{11}$).

Example 5—X-Ray Crystallography Experimental Details

X-ray crystal structure data was collected from multi-faceted crystals of suitable size and quality selected from a representative sample of crystals of the same habit using an optical microscope. In each case, crystals were mounted on MiTiGen loops with data collection earned out in a cold stream of nitrogen (150 K; Bruker D8 QUEST ECO). All diffractometer manipulations were carried out using Bruker APEX3 software (26). Structure solution and refinement was carried out using XS, XT and XL software, embedded within the Bruker SHELXTL suite (27). For each structure, the absence of additional symmetry was confirmed using ADDSYM incorporated in the PLATON program (28).

Crystal structure data for L1: X-ray quality crystals were grown following diffusion of diethylether vapor into CHCl$_3$ at room temperature. Crystal structure parameters: C$_{22}$H$_{24}$N$_2$O$_1$ 332.43 g/mol, triclinic, space group P2$_1$/c; a=13.0840(8) Å, b=15.8238(9) Å, c=8.6839(5) Å, or α=γ=90°, β=98.385(3)°, V=1778.68(18) Å$^3$; Z=4, ρ$_{calcd}$=1.241 g cm$^{-3}$; crystal dimensions 0.300×0.100×0.090 mm; diffractometer Bruker D8 QUEST ECO CMOS; Mo K$_\alpha$ radiation, 150(2) K, 2θ$_{max}$=2.698 to 27.568°; reflections, 4082 independent (R$_{int}$=0.0479), direct methods; absorption coeff (μ=0.076 mm$^{-1}$), absorption correction semi-empirical from equivalents (SADABS); refinement (against F$_o^2$) with SHELXTL V6.1, 231 parameters, 0 restraints, R$_1$=0.0594 (I>2σ) and wR$_2$=0.1499 (all data), Goof=1.101, residual electron density 0.266/−0.245 e Å$^{-3}$.

Crystal structure data for 1: X-ray quality crystals were grown following diffusion of diethylether vapor into CHCl$_3$ at room temperature. Crystal structure parameters: C$_{23}$H$_{24}$Cl$_4$N$_2$O$_1$Pt$_1$ 681.33 g/mol, monoclinic, space group P2$_1$/n; a=6.9467(3) Å, b=18.7502(6) Å, c=18.4435(6) Å, α=γ=90°, β=100.0770(10)°, V=2365.24(15) Å$^3$; Z=4, ρ$_{calcd}$=1.913 g cm$^{-3}$; crystal dimensions 0.150×0.059×0.047 mm; diffractometer Bruker D8 QUEST ECO CMOS; Mo K$_\alpha$ radiation, 150(2) K, 2θ$_{max}$=2.243 to 27.535°; 44379 reflections, 5419 independent (R$_{int}$=0.0646), direct methods; absorption coeff (μ=6.403 mm$^{-1}$), absorption correction semi-empirical from equivalents (SADABS); refinement (against F$_o^2$) with SHELXTL V6.1, 285 parameters, restraints, R$_1$=0.0326 (I>2σ) and wH$_2$=0.0677 (all data), Goof=1.075, residual electron density 1.442/−1.154 e Å$^{-3}$.

Example 6—Optical Spectroscopy Measurements

All measurements were obtained at 25° C. The absorption spectra of the ligands and complexes were measured in solution in 1 cm quartz cuvettes using a Cary 5000 UV-Vis-NIR spectrophotometer. Emission spectra were recorded in 1 cm quartz cuvettes using PTI Quantamaster 30 spectrophotometer. Different solvents were employed to test for solvatochromism. Quantum yields were measured using the following standards: Ru(bpy)$_3$Cl$_2$ (in deionized H$_2$O) for the complexes (λ$_{exc}$=450 nm, band pass=3 nm).

Example 7—Theoretical Calculations

Figure 11:
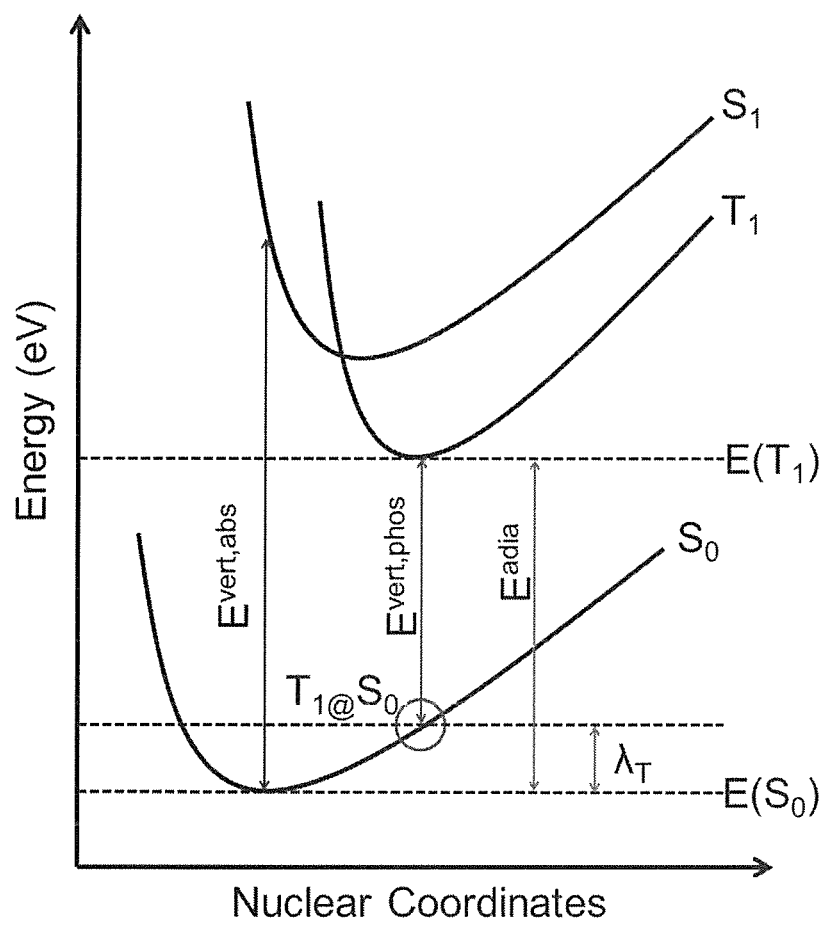
FIG. 11. Figure from theoretical calculations.
Figure 12:
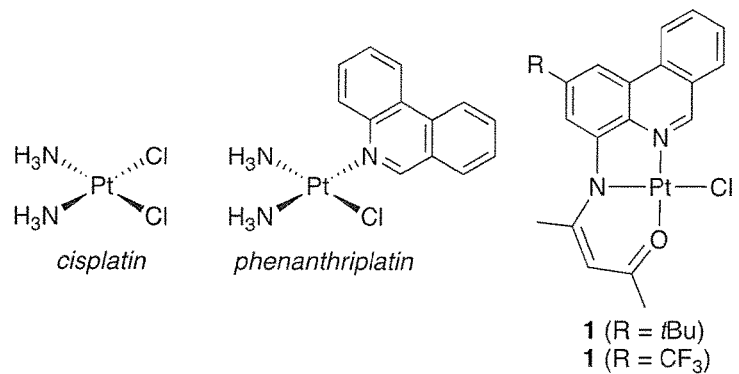
FIG. 12. Structures of the clinically approved bifunctional platinum anticancer drug cisplatin, a leading monofunctional drug candidate phenanthriplatin (10), and the planar phenanthridine-containing platinum complexes described in this study.

Electronic calculations. All DFT and TD-DFT calculations were performed using Gaussian 09, Revision B.09 with the M06 functional, all electron basis sets for the main-group elements, and the SDD effective core potential with the corresponding basis set for Pt. Frequency calculations were performed to confirm all optimized structures are at a minimum. Effects of solvation were included using the SMD model with CH$_2$Cl$_2$ as solvent. UV-Vis spectra were simulated and analyzed using GaussSum. MO population analysis was performed with Multiwfn. Photophysical parameters were obtained as follows: 1) E$^{vert-abs}$ with TD-DFT singlet-singlet vertical excitation, 2) E$^{vert, phos}$ as the difference between the single point energies between E(T$_1$) and E(T$_1$@S$_0$), and 3) λ$_T$ as the difference between the single point energies between E(T$_1$@S$_0$) and E(S$_0$). (See FIG. 11)

Example 8—MTT Assays

Materials
Cell line: A2780 (ovarian cells), A2780cis (ovarian cells, drug resistant)
RPMI medium: 10% FBS, 1% PS, 89% RPMI 1×, with L-glutamine
MTT (5 mg/Ml Thiazolyl Blue tetrazolium bromide in PBS)
Dimethyl sulfoxide (DMSO)
Method
A volume of 100 μL of RPMI medium (10% FBS, 1% PS, 89% RPMI 1×, with L-glutamine) containing 2000 cells was seeded in each well of a 96-well microplate, and incubated for 24 h at 37° C. under 5% CO$_2$. After 24 h, a volume of 50 μL of media containing the new compounds of different concentrations was added to the well. The drug-treated cells were incubated for 72 h at 37° C. with 5% CO$_2$. A volume of 30 μL media containing MTT was added into each well, and incubated for 2-4 h at 37° C. with 5% CO$_2$. MTT would be reduced to formazan in living cells.

Following this, the media were removed carefully by aspiration and 200 μL DMSO was added into each well. The DMSO is used to dissolve the insoluble formazan into a purple solution. The 96-well microplate with DMSO was then shaken for 10 min at room temperature. Final results were obtained by using a microplate reader to examine the absorbance at 562 nm. Analysis of the data was carried out using Origin™.

Example 8—Cell Cultures

A2780 and A2780cis cell lines were cultured in RPM11640 with L-glutamine supplemented with 10% FBS and 1% PS. SKOV-3, MDA-MB-231, A549, and HEK293 cell line were cultured in DMEM 1 g/L glucose, with L-glutamine & sodium pyruvate supplemented with 10% FBS and 1% PS. MET5A cell line was cultured in M199 supplemented with 10% FBS, 1% PS, insulin, 0.1% Trace Elements B, 4 mM Hydrocortisone, and 4 ng/mL EGF. All cell lines were incubated at 37° C. under an atmosphere containing 5% $CO_2$. Cells were passaged by trypsinization and split in a 1:5 ratio.

Example 9—Uptake

SKOV-3 cells were plated in a 6-well and at 37° C. under an atmosphere containing 5% $CO_2$ for 24 hr. Cells were then treated with 2 μM Pt compound for 24 hr. After incubation with Pt, cells were collected by trypsinization and washed with 1 mL PBS. Cells were counted, recollected, and resuspended in 200 μL 65% nitric acid. Samples were stored shaking at room temperature overnight. After the cell pellet was dissolved, the solutions were diluted with water and analyzed by GFAAS. All experiments were performed in triplicate.

Example 10—Apoptosis

SKOV-3 cells were seeded in a 6-well plate at a concentration of $4\times10^5$ cells/well. Cells were then incubated at 37° C. under an atmosphere containing 5% $CO_2$ for 24 hr. Cells were treated with compound for 72 hr (15 μM cisplatin, 1 μM phenanthriplatin, 1 μM 2). Cells were harvested, the supernatant was then discarded, and cells were resuspended in 1 mL PBS. Cells were resuspended in 1× binding buffer using the FITC Annexin V Apoptosis Detection Kit 1 (BD Biosciences, Franklin Lakes, N.J., USA) reaching a concentration of $10^6$ cells/mL. 100 μL of this cell solution was transferred to a 5 mL culture tube. Then, 5 μL of Annexin V-FITC and 10 μL propidium iodide (PI) solutions were added to cells. Cells were incubated for 15 min at RT in the dark and then brought to a final volume of 400 μL with 1× binding buffer. Cells were then analyzed with FITC and PerCP-Cy5-5 channels on FACSAria™ II (BD Biosciences, Franklin Lakes, N.J., USA) and data was processed using FlowJo software.

The scope of the claims should not be limited by the preferred embodiments set forth in the examples but should be given the broadest interpretation consistent with the description as a whole.

TABLE 1

Photophysical properties of ligands and NNOPt complexes.

| Compounds | $\lambda_{abs,max}$ (nm)$^a$ | $\lambda_{em,max}$ (nm)$^a$ | $\Phi_P{}^b$ |
|---|---|---|---|
| L1 | 317, 359 | 460 | — |
| L2 | 316, 364 | 460 | — |
| 1 | 357, 461 | 603 | 0.11 |
| 2 | 353, 474 | 604 | 0.21 |

$^a$Solutions in $CH_2Cl_2$ (100 μM).
$^b$Photoluminescence quantum yield using Ru(bpy)$_3$Cl$_2$ in aerated deionized water as standard ($\lambda_{exc}$ = 450 nm, $\Phi_{P,ref}$ = 0.040, band pass = 3 nm).

TABLE 2

Preliminary cytotoxicity assay data.

| Drugs | A2780 IC50 (μM) | A2780cis IC50 (μM) |
|---|---|---|
| cisplatin | 0.375 ± 0.217 | 7.76 ± 0.497 |
| 1 | 2.81 ± 0.168 | 4.57 ± 1.41 |
| 2 | 0.341 ± 0.112 | 0.955 ± 0.106 |
| 2-tBu | 8.38 ± 2.83 | 20.5 ± 6.07 |
| 2-CF$_3$ | 19.3 ± 12.1 | >100 μM |
| L2 | 7.22 ± 2.07 | 20.1 ± 7.17 |

TABLE 3

Photophysical properties of L1-L2 and platinum complexes 1-2.

| Compound | $\lambda_{abs,max}$ (nm)$^a$ | $\lambda_{em,max}$ (nm)$^a$ | $\phi_P{}^b$ |
|---|---|---|---|
| L1 | 317, 359 | 460 | — |
| L2 | 316, 364 | 460 | — |
| 1 | 357, 461 | 603 | 0.11 |
| 2 | 353, 474 | 604 | 0.21 |

$^a$Solutions in $CH_2Cl_2$ (100 μM).
$^b$Photoluminescence quantum yield using Ru(bpy)$_3$Cl$_2$ in aerated deionized water as standard ($\lambda_{exc}$ = 450 nm, $\phi_{P,ref}$ = 0.040, band pass = 3 nm).

REFERENCES

1. Wheate, N. J.; Walker, S.; Craig, G. E.; Oun, R. The status of platinum anticancer drugs in the clinic and in clinical trials. *Dalton Transactions* 2010, 39, 8113-8127.
2. Rosenberg, B.; VanCamp, L.; Trosko, J. E.; Mansour, V. H. Platinum compounds: a new class of potent antitumour agents. *Nature* 1969, 222, 385-6.
3. Kelland, L. The resurgence of platinum-based cancer chemotherapy. *Nat Rev. Cancer* 2007, 7, 573-584.
4. Dhar, S.; Lippard, S. J. In *Current status and mechanism of action of platinum-based anticancer drugs*, 2011; Wiley-VCH Veriag GmbH & Co. KGaA: 2011; pp 79-95.
5. Johnstone, T. C.; Park, G. Y.; Lippard, S. J. Understanding and improving platinum anticancer drugs—phenanthriplatin. *Anticancer Res.* 2014, 34, 471-476.
6. Todd, R. C.; Lippard, S. J. Structure of duplex DNA containing the cisplatin 1,2-{Pt(NH3)2}2+-d(GpG) crosslink at 1.77 Å resolution. *J. Inorg. Biochem.* 2010, 104, 902-908.
7. Johnstone, T. C.; Wilson, J. J.; Lippard, S. J. Monofunctional and higher-valent platinum anticancer agents. *Inorg. Chem.* 2013, 52, 12234-12249.
8. Lovejoy, K. S.; Todd, R. C.; Zhang, S.; McCormick, M. S.; D'Aquino, J. A.; Reardon, J. T.; Sancar, A.; Giacomini, K. M.; Lippard, S. J. cis-diammine(pyridine)chloroplatinum(II), a monofunctional platinum(II) antitumor agent: uptake, structure, function, and prospects. *Proc. Natl. Acad. Sci. U.S.A* 2008, 105, 8902-8907.

9. Lovejoy, K. S.; Serova, M.; Bieche, I.; Emami, S.; D'Incalci, M.; Broggini, M.; Erba, E.; Gespach, C.; Cvitkovic, E.; Faivre, S.; Raymond, E.; Lippard, S. J. Spectrum of Cellular Responses to Pyriplatin, a Monofunctional Cationic Antineoplastic Platinum(II) Compound, in Human Cancer Cells. *Mol. Cancer Ther.* 2011, 10, 1709-1719.

10. Park, G. Y.; Wilson, J. J.; Song, Y.; Lippard, S. J. Phenanthriplatin, a monofunctional DNA-binding platinum anticancer drug candidate with unusual potency and cellular activity profile. *Proc. Natl. Acad. Sci. U.S.A* 2012, 109, 11987-11992, S11987/1-S11987/24.

11. Lippand, S. J.; Park, G. Y.; Johnstone, T.; Farokhzad, O. C.; Gadde, S. Compositions comprising platinum compounds associated with polymers and methods for the treatment of cancer. WO2012177935A1, 2012.

12. Bilodeau, M. T.; Dunbar, C. A.; Barder, T. E.; Lee, E. R.; Alargova, R. G.; Rockwood, D. N.; Moreau, B.; Shinde, R.; Bouthillette, M. Preparation of platinum(II) chloro ammine complexes with derivs. of quinoline, benzimidazole, and phenanthridine for the treatment of cancer. WO2014043243A2, 2014.

13. Johnstone, T. C.; Alexander, S. M.; Lin, W.; Lippard, S. J. Effects of monofunctional platinum agents on bacterial growth: a retrospective study. *J. Am. Chem. Soc.* 2014, 136, 116-118.

14. Gray, H. B. Molecular orbital theory for transition metal complexes. *Journal of Chemical Education* 1964, 41, 2.

15. Johnstone, T. C.; Lippard, S. J. The Chiral Potential of Phenanthriplatin and Its Influence on Guanine Binding. *J. Am. Chem. Soc.* 2014, 136, 2126-2134.

16. Mondal, R.; Giesbrecht, P. K.; Herbert, D. E. Nickel(II), copper(I) and zinc(II) complexes supported by a (4-diphenylphosphino)phenanthridine ligand. *Polyhedron* 2016, 108, 156-162.

17. Mandapati, P.; Giesbrecht, P. K.; Davis, R. L.; Herbert, D. E. Phenanthridine-Containing Pincer-like Amido Complexes of Nickel, Palladium, and Platinum. *Inorg. Chem.* 2017, 56, 3674-3685.

18. Mondal, R.; Lozada, I. B.; Davis, R. L.; Williams, J. A. G.; Herbert, D. E. Site-Selective Benzannulation of N-Heterocycles in Bidentate Ligands Leads to Blue-Shifted Emission from [(P N)Cu]2(μ-X)2 Dimers. *Inorg. Chem.* 2018, 57, 4966-4978.

19. Le, P. J. B. Use of ethidium bromide for separation and determination of nucleic acids of various conformational forms and measurement of their associated enzymes. *Methods Biochem Anal* 1971, 20, 41-86.

20. Tumir, L.-M.; Stojkovic, M. R.; Piantanida, I. Comeback of phenanthridine and phenanthridinium derivatives in the 21st century. *Beilstein J. Org. Chem.* 2014, 10, 2930-2954, 25 pp.

21. Walker, M. C.; Chang, M. C. Y. Natural and engineered biosynthesis of fluorinated natural products. *Chem. Soc. Rev.* 2014, 43, 6527-6536.

22. O'Ferrall, R. A. M.; Murray, B. A. 1H and 13C NMR spectra of α-heterocyclic ketones and assignment of keto, enol and enaminone tautomeric structures. *J. Chem. Soc., Perkin Trans.* 21994, 2461-70.

23. Macrae, C. F.; Bruno, I. J.; Chisholm, J. A.; Edgington, P. R.; McCabe, P.; Pidcock, E.; Rodriguez-Monge, L.; Taylor, R.; van de Streek, J.; Wood, P. A. Mercury CSD 2.0—New Features for the Visualization and Investigation of Crystal Structures. *Journal of Applied Crystallography* 2008, 41, 466-470.

24. Kalinowski, J.; Fattori, V.; Cocchi, M.; Williams, J. A. G. Light-emitting devices based on organometallic platinum complexes as emitters. *Coord. Chem. Rev.* 2011, 255, 2401-2425.

25. Vemekar, A. A.; Berger, G.; Czapar, A. E.; Veliz, F. A.; Wang, D. I.; Steinmetz, N. F.; Lippard, S. J. Speciation of phenanthriplatin and its analogs in the core of Tobacco Mosaic Virus. *J. Am. Chem. Soc.* 2018, 140, 4279-4287.

26. Bruker-AXS *APEX*3 v2016.1-0, Madison, Wis., USA, 2016.

27. Sheldrick, G. M. A Short History of SHELX. *Acta Cryst.* 2008, A64, 112-122.

28. Spek, A. L. Structure Validation in Chemical Crystallography. *Acta Cryst.* 2009, D65, 148-155.

29. Wang, D.; Lippard, S. J. Cellular Processing of Platinum Anticancer Drugs. *Nature Reviews Drug Discovery* 2005, 4, 307-320.

30. Almaqwashi, A. A.; Zhou, W.; Naufer, M. N.; Riddell, I. A.; Yilmaz, 0. H.; Lippard, S. J.; Williams, M. C. DNA Intercalation Facilitates Efficient DNA-Targeted Covalent Binding of Phenanthriplatin. *J. Am. Chem. Soc.* 2019, 141, 1537-1545.

31. Zhou, W.; Almeqdadi, M.; Xifaras, M. E.; Riddell, I. A.; Yilmaz, Ö. H.; Lippard, S. J. The effect of geometric isomerism on the anticancer activity of the monofunctional platinum complex trans-[Pt(NH$_3$)$_2$(phenanthridine)Cl]NO3. *Chem. Commun.* 2018, 54, 2788-2791.

32. Chua, E. Y. D.; Davey, G. E.; Chin, C. F.; Droge, P.; Ang, W. H.; Davey, C. A. Stereochemical control of nucleosome targeting by platinum-intercalator antitumor agents. *Nucleic Acids Research* 2015, 43, 5284-5296.

33. Dabrowiak, J. C., Platinum Anticancer Drugs. In *Metals in Medicine*, Wiley: Hoboken, 2009; pp 109-147.

34. Wu, X.; Sun, X.; Guo, Z.; Tang, J.; Shen, Y.; James, T. D.; Tian, H.; Zhu, W. In Vivo and in Situ Tracking Cancer Chemotherapy by Highly Photostable NIR Fluorescent Theranostic Prodrug. *J. Am. Chem. Soc.* 2014, 136, 3579-3588.

35. Leucuta, S. E. Subcellular Drug Targeting, Pharmacokinetics and Bioavailability. *J. Drug Targeting* 2014, 22, 95-115.

36. Liang, D.; Wu, X.; Hasinoff, B.; Herbert, D. E.; Tranmer, G. Evaluation of Nitrobenzyl Derivatives of Camptothecin as Anti-Cancer Agents and Potential Hypoxia Targeting Prodrugs. *Molecules* 2018, 23, 2041-2057.

37. Braun, J. D.; Lozada, I. B.; Kolodziej, C.; Burda, C.; Davis, R. L.; Newman, K. M. E.; van Lierop, J.; Herbert, D. E. Iron Coordination Complexes with Pan-Chromatic Absorption and Nanosecond Charge-Transfer Excited State Lifetimes, *under revision* 2019.

38. Johnstone, T. C. The crystal structure of oxaliplatin: A case of overlooked pseudo symmetry. *Polyhedron* 2014, 67, 429-435.

39. Dabrowiak, J. C., Platinum Anticancer Drugs. In *Metals in Medicine*, Wiley: Hoboken, 2009; 109-147.

40. Park, G. Y.; Wilson, J. J.; Song, Y.; Lippard, S. J. Phenanthriplatin, a monofunctional DNA-binding platinum anticancer drug candidate with unusual potency and cellular activity profile. Proc. Natl. Acad. Sci. U.S.A 2012, 109, 11987-11992, S11987/1-S11987/24.

41. Botchway, S. W.; Chamley, M.; Haycock, J. W.; Parker, A. W.; Rochester, D. L.; Weinstein, J. A.; Williams, J. A. G. Time-resolved and two-photon emission imaging microscopy of live cells with inert platinum complexes. Proceedings of the National Academy of Sciences 2008, 105, 16071-16076.

42. Pan, D.; she, W.; Guo, C.; Luo, K.; Yi, Q.; Gu, Z. PEGylated dendritic diaminocyclohexyl-platinum (II) conjugates as pH-responsive drug delivery vehicles with enhanced tumor accumulation and antitumor efficacy. Biomaterials 2014, 35, 10080-10092.

43. Prabhakar, U.; Maeda, H.; Jain, R. K.; Sevick-Muraca, E. M.; Zamboni, W.; Farokhzad, O. C.; Barry, S. T.; Gabizon, A.; Grodzinski, P.; Blakey, D. C. Challenges and Key Considerations of the Enhanced Permeability and Retention Effect for Nanomedicine Drug Delivery in Oncology. Cancer Res. 2013, 73, 2412-2417.

44. Bertrand, N.; Wu, J.; Xu, X.; Kamaly, N.; Farokhzad, O. C. Cancer nanotechnology: The impact of passive and active targeting in the era of modern cancer biology. Adv. Drug Delivery Rev. 2014, 66, 2-25.

45. Johnstone, T. C.; Wilson, J. J.; Lippard, S. J. Monofunctional and higher-valent platinum anticancer agents. Inorg. Chem. 2013, 52, 12234-12249.

46. Barnes, K. R.; Kutikov, A.; Lippard, S. J. Synthesis, Characterization, and Cytotoxicity of a Series of Estrogen-Tethered Platinum(IV) Complexes. Chem. Biol. 2004, 11, 557-564.

The invention claimed is:

1. An anti-cancer compound comprising a compound of formula (I):

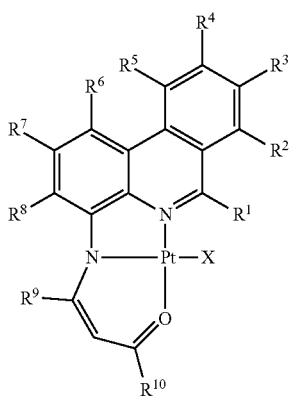

(I)

wherein:
X is a halide, a nitrate, a carboxylate or an anionic ligand;
$R^1$-$R^8$ are individually H, tBu, $CH_3$, $CF_3$, Cl, Br, F, C(O)H or OR, where R is an alkyl or aryl; and
$R^9$ and $R^{19}$ are individually H, $CF_3$ or $CH_3$.

2. The anti-cancer compound according to claim 1 wherein $R^1$-$R^6$ and $R^8$=H, $R^7$=$CF_3$ or tBu, and $R^9$-$R^{10}$=$cH_3$.

3. The anti-cancer compound according to claim 1 wherein $R^1$=$R^7$=$CH_3$, $R^{2-6}$=$R^8$=H.

4. The anti-cancer compound according to claim 1 wherein $R^{1-8}$=H.

5. The anti-cancer compound according to claim 1 wherein $R^7$=C(=O)H (aldehyde), $R^{1-6}$=$R^8$=H.

6. The anti-cancer compound according to claim 1 wherein the anti-cancer compound is selected from the group consisting of: $R^7$=Su; $R^7$=$CF_3$; $R^7$=$CH_3$; $R^1$=$CH_3$, =$CH_3$, $R^{10}$=$CH_3$; $R^1$=H, $R^7$=$R^{10}$=$CF_3$; and $R^1$=H, $R^7$=$CF_3$, $R^{10}$=$CF_3$.

7. A method of modifying a compound of formula (I) as set forth in claim 1 comprising:
providing a compound of formula (I) wherein at least one of $R^1$-$R^8$ is $CH_3$; and
subjecting the compound to oxidizing conditions such that the at least one $CH_3$ is converted to C(O)H.

8. The method according to claim 7 further comprising, following subjection to the oxidizing conditions, converting the C(O)H to an amide group, a carboxylic acid group or an ester group.

9. The method according to claim 8 further comprising, following conversion, conjugating targeting tag to the compound via the amide group, the carboxylic acid group or the ester group.

10. The method according to claim 9 wherein the targeting tag is a protein, a peptide tag, a DNA molecule, an oligonucleotide or an siRNA.

11. A method of treating cancer comprising administering to an individual in need of such treatment an effective amount of an anti-cancer compound as set forth in claim 1.

12. The method according to claim 11 wherein the compound is co-administered with a second anti-cancer drug.

13. The method according to claim 12 wherein the second anti-cancer drug is selected from the group consisting of: fluorouracil, etoposide, paclitaxel, leucovorin and capecitabine.

14. The method according to claim 11 wherein the cancer is selected from the group consisting of anal cancer, bladder cancer, cervical cancer, esophageal cancer, gastric cancer, head and neck cancer, non-small cell lung cancer, small cell lung cancer, ovarian cancer, prostate cancer, testicular cancer, thymic cancer, neuroendocrine cancer, soft tissue sarcoma, breast cancer, endometrial cancer, thyroid cancer, melanoma and colorectal cancer.

* * * * *